(12) United States Patent
Aagaard et al.

(10) Patent No.: US 10,641,770 B2
(45) Date of Patent: May 5, 2020

(54) DIAGNOSTIC REAGENTS FOR IMPROVED IN VIVO OR IN VITRO CELL-MEDIATED IMMUNOLOGICAL DIAGNOSIS OF TUBERCULOSIS

(71) Applicant: STATENS SERUM INSTITUT, Copenhagen S (DK)

(72) Inventors: Claus Aagaard, Copenhagen S (DK); Søren Tetens Hoff, Copenhagen V (DK); Ida Rosenkrands, Værløse (DK); Else Marie Agger, Copenhagen S (DK); Peter Lawætz Andersen, Brønshøj (DK)

(73) Assignee: Statens Serum Institut, Copenhagen (DK)

( * ) Notice: Subject to any disclaimer, the term of this patent is extended or adjusted under 35 U.S.C. 154(b) by 175 days.

(21) Appl. No.: 15/104,957

(22) PCT Filed: Dec. 15, 2014

(86) PCT No.: PCT/DK2014/000062
§ 371 (c)(1),
(2) Date: Jun. 15, 2016

(87) PCT Pub. No.: WO2015/090322
PCT Pub. Date: Jun. 25, 2015

(65) Prior Publication Data
US 2017/0016897 A1 Jan. 19, 2017

(30) Foreign Application Priority Data
Dec. 16, 2013 (DK) .................................. 2013 00698

(51) Int. Cl.
*A61K 39/00* (2006.01)
*A61K 39/02* (2006.01)
*A61K 39/04* (2006.01)
*G01N 33/569* (2006.01)

(52) U.S. Cl.
CPC ..... *G01N 33/5695* (2013.01); *G01N 2469/20* (2013.01)

(58) Field of Classification Search
CPC ................................ A61K 39/00; A61K 39/04
USPC .................... 424/184.1, 185.1, 234.1, 248.1
See application file for complete search history.

(56) References Cited

FOREIGN PATENT DOCUMENTS

| WO | WO 2010/115989 A1 | 10/2010 | |
|----|----|----|----|
| WO | WO2010/121618 * | 10/2010 | ............. A61K 39/04 |
| WO | WO 2012/011144 A2 | 1/2012 | |
| WO | WO 2012/057904 A1 | 5/2012 | |
| WO | WO 2012/167307 A1 | 12/2012 | |

OTHER PUBLICATIONS

Aagaard, C., I. Brock, et al. (Mar. 1, 2004). Mapping immune reactivity toward Rv2653 and Rv2654: two novel low-molecular-mass antigens found specifically in the Mycobacterium tuberculosis complex. The Journal of infectious diseases 189(5): 812-819.
Aagaard, C., T. Hoang, et al. (Jan. 23, 2011). A multistage tuberculosis vaccine that confers efficient protection before and after exposure. Nature medicine 17(2): 189-194.
Abdallah, A. M., N. C. Gey Van Pittius, et al. (Oct. 8, 2007). Type VII secretion—mycobacteria show the way. Nature reviews. Microbiology 5(11): 883-891.
Aggerbeck, H., R. Giemza, et al. (May 14, 2013). Randomised clinical trial investigating the specificity of a novel skin test (C-Tb) for diagnosis of M. tuberculosis infection. PloS one 8(5): e64215.
Albrethsen, J., J. Agner, et al. (Jan. 23, 2013). Proteomic profiling of Mycobacterium tuberculosis identifies nutrient-starvation-responsive toxin-antitoxin systems. Molecular & cellular proteomics : MCP 12(5): 1180-1191.
Andersen, P. (Mar. 31, 1994). Effective vaccination of mice against Mycobacterium tuberculosis infection with a soluble mixture of secreted mycobacterial proteins. Infection and immunity 62(6): 2536-2544.
Andersen, P., M. E. Munk, et al. (Sep. 23, 2000). Specific immune-based diagnosis of tuberculosis. Lancet 356(9235): 1099-1104.
Arnvig, K. B., I. Comas, et al. (Nov. 3, 2011). Sequence-based analysis uncovers an abundance of non-coding RNA in the total transcriptome of Mycobacterium tuberculosis. PLoS pathogens 7(11): e1002342.
Behr, M. A., M. A. Wilson, et al. (May 28, 1999). Comparative genomics of BCG vaccines by whole-genome DNA microarray. Science 284(5419): 1520-1523.
Biselli, R., S. Mariotti, et al. (Aug. 8, 2010). Detection of interleukin-2 in addition to interferon-γ discriminates active tuberculosis patients, latently infected individuals, and controls. Clinical Microbiology and Infection 16(8): 1282-1284.
Brock, I., K. Weldingh, et al. (Jun. 2004). Specific T-cell epitopes for immunoassay-based diagnosis of Mycobacterium tuberculosis infection. Journal of clinical microbiology 42(6): 2379-2387.
Chen, J. M., S. Boy-Rottger, et al. (Feb. 2012). EspD is critical for the virulence-mediating Esx-1 secretion system in Mycobacterium tuberculosis. Journal of bacteriology 194(4): 884-893.
De Souza, G. A., M. O. Arntzen, et al. (Oct. 28, 2010). Proteogenomic analysis of polymorphisms and gene annotation divergences in prokaryotes using a clustered mass spectrometry-friendly database. Molecular & cellular proteomics : MCP 10(1): M110 002527.
Deenadayalan, A., D. Heaslip, et al. (Dec. 22, 2009). Immunoproteomic identification of human T cell antigens of Mycobacterium tuberculosis that differentiate healthy contacts from tuberculosis patients. Molecular & cellular proteomics : MCP 9(3): 538-549.
Dewan, P. K., J. Grinsdale, et al. (Nov. 28, 2006). Low Sensitivity of a Whole-Blood Interferon-γ Release Assay for Detection of Active Tuberculosis. Clinical Infectious Diseases 44(1): 69-73.

(Continued)

*Primary Examiner* — Rodney P Swartz
(74) *Attorney, Agent, or Firm* — Duminiak Law, LLC

(57) ABSTRACT

The present invention discloses in vitro and in vivo diagnostic methods with enhanced specificity and sensitivity for the detection of tuberculosis. The diagnostic reagents of the present invention can replace former mixtures/cocktails/pools of antigens comprising ESAT-6 but including ESAT6 improves the diagnosis even further.

Figure 1:
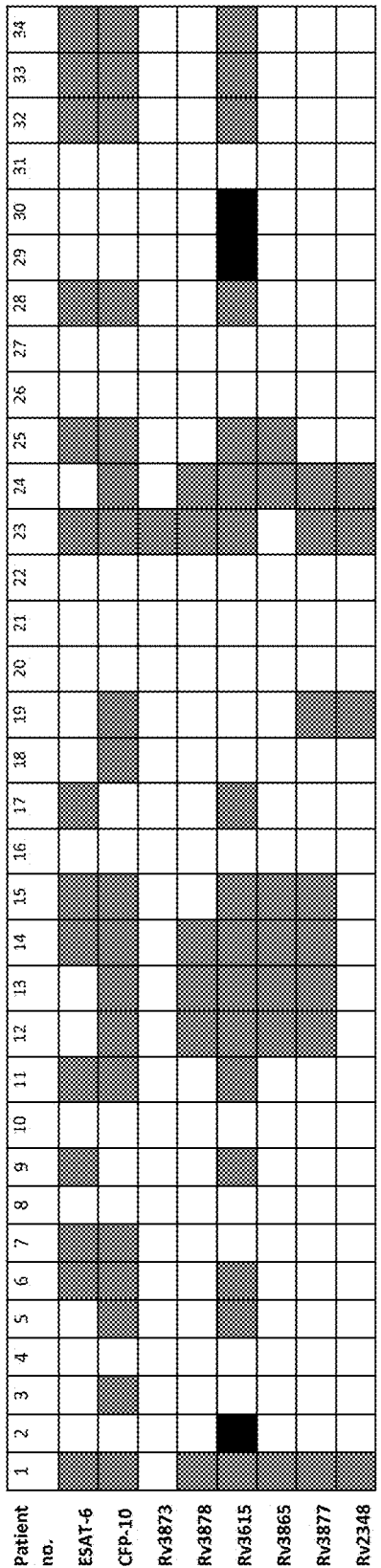

16 Claims, 8 Drawing Sheets
Specification includes a Sequence Listing.

(56) References Cited

OTHER PUBLICATIONS

Ewer, K., P. Cockle, et al. (Nov. 9, 2005). Antigen mining with iterative genome screens identifies novel diagnostics for the Mycobacterium tuberculosis complex. Clinical and vaccine immunology : CVI 13(1): 90-97.

Fortune, S. M., A. Jaeger, et al. (Jun. 13, 2005). Mutually dependent secretion of proteins required for mycobacterial virulence. Proceedings of the National Academy of Sciences of the United States of America 102(30): 10676-10681.

Hall, L. J., S. Clare, et al. (Sep. 1, 2009). Characterisation of a live Salmonella vaccine stably expressing the Mycobacterium tuberculosis Ag85B-ESAT-6ESAT-6 fusion protein. Vaccine 27(49): 6894-6904.

Harboe, M., A. S. Malin, et al. (Feb. 1998). B-cell epitopes and quantification of the ESAT-6 protein of Mycobacterium tuberculosis. Infection and immunity 66(2): 717-723.

Kilgus, J., T. Jardetzky, et al. (Jan. 1, 1991). Analysis of the permissive association of a malaria T cell epitope with DR molecules. The Journal of Immunology 146(1): 307-315.

Liu, X. Q., D. Dosanjh, et al. (May, 2004). Evaluation of T-cell responses to novel RD1- and RD2-encoded Mycobacterium tuberculosis gene products for specific detection of human tuberculosis infection. Infection and immunity 72(5): 2574-2581.

Lustig, J. V., H. L. Rieger, et al. (Mar. 4, 1976). Humoral and cellular responses to native antigen following oral and parenteral immunization with lipid-conjugated bovine serum albumin. Cellular immunology 24(1): 164-172.

MacGurn, J. A., S. Raghavan, et al. (Jun. 28, 2005). A non-RD1 gene cluster is required for Snm secretion in Mycobacterium tuberculosis. Molecular microbiology 57(6): 1653-1663.

Merrifield, R. B. (Jun. 20, 1963). Solid Phase Peptide Synthesis. I. The Synthesis of a Tetrapeptide. Journal of the American Chemical Society 85(14): 2149-2154.

Millington, K. A., S. M. Fortune, et al. (Feb. 18, 2011). Rv3615c is a highly immunodominant RD1 (Region of Difference 1)-dependent secreted antigen specific for Mycobacterium tuberculosis infection. Proceedings of the National Academy of Sciences of the United States of America 108(14): 5730-5735.

Mowat, A. M., A. M. Donachie, et al. (Nov. 7, 1990). Immune-stimulating complexes containing Quil A and protein antigen prime class I MHC-restricted T lymphocytes in vivo and are immunogenic by the oral route. Immunology 72(3): 317-322.

Mustafa, A. S., R. Al-Attiyah, et al. (Jun. 2008). Efficient testing of large pools of Mycobacterium tuberculosis RD1 peptides and identification of major antigens and immunodominant peptides recognized by human Th1 cells. Clinical and vaccine immunology: CVI 15(6): 916-924.

Nagai, S., H. G. Wiker, et al. (Jan. 1991). Isolation and partial characterization of major protein antigens in the culture fluid of Mycobacterium tuberculosis. Infection and immunity 59(1): 372-382.

Pai, M., L. W. Riley, et al. (Dec. 2004). Interferon-gamma assays in the immunodiagnosis of tuberculosis: a systematic review. The Lancet infectious diseases 4(12): 761-776.

Pearson, W. R. and D. J. Lipman (Apr. 1988). Improved tools for biological sequence comparison. Proceedings of the National Academy of Sciences 85(8): 2444-2448.

Ravn, P., A. Demissie, et al. (Oct. 21, 1998). Human T Cell Responses to the ESAT-6 Antigen from Mycobacterium tuberculosis. Journal of Infectious Diseases 179(3): 637-645.

Redelman-Sidi, G. and K. A. Sepkowitz (Dec. 21, 2013). IFN-gamma release assays in the diagnosis of latent tuberculosis infection among immunocompromised adults. American journal of respiratory and critical care medicine 188(4): 422-431.

Rosenkrands, I., P. B. Rasmussen, et al. (Jun. 1998). Identification and characterization of a 29-kilodalton protein from Mycobacterium tuberculosis culture filtrate recognized by mouse memory effector cells. Infection and immunity 66(6): 2728-2735.

Schopfer, K., H. L. Rieder, et al. (Sep. 25, 2013). The sensitivity of an interferon-gamma release assay in microbiologically confirmed pediatric tuberculosis. European journal of pediatrics.

Sester, U., M. Fousse, et al. (Mar. 15, 2011). Whole-Blood Flow-Cytometric Analysis of Antigen-Specific CD4 T-Cell Cytokine Profiles Distinguishes Active Tuberculosis from Non-Active States. PloS one 6(3): e17813.

Sidders, B., C. Pirson, et al. (Sep. 2008). Screening of highly expressed mycobacterial genes identifies Rv3615c as a useful differential diagnostic antigen for the Mycobacterium tuberculosis complex. Infection and immunity 76(9): 3932-3939.

Sinigaglia, F., M. Guttinger, et al. (Dec. 1988). A malaria T-cell epitope recognized in association with most mouse and human MHC class II molecules. Nature 336(6201): 778-780.

Skjot, R. L., T. Oettinger, et al. (Jan. 2000). Comparative evaluation of low-molecular-mass proteins from Mycobacterium tuberculosis identifies members of the ESAT-6 family as immunodominant T-cell antigens. Infection and immunity 68(1): 214-220.

Sonnenberg, P., J. R. Glynn, et al. (Jan. 15, 2005). How soon after infection with HIV does the risk of tuberculosis start to increase? a retrospective cohort study in South African gold miners. The Journal of infectious diseases 191(2): 150-158.

Stryhn, A., L. Ø. Pedersen, et al. (Jun. 3, 1996). Peptide binding specificity of major histocompatibility complex class I resolved into an array of apparently independent subspecificities: quantitation by peptide libraries and improved prediction of binding. European Journal of Immunology 26(8): 1911-1918.

Thompson, J. D., D. G. Higgins, et al. (Sep. 23, 1994). Clustal W: improving the sensitivity of progressive multiple sequence alignment through sequence weighting, position-specific gap penalties and weight matrix choice. Nucleic Acids Research 22(22): 4673-4680.

Van Dissel, J. T., S. M. Arend, et al. (Mar. 11, 2010). Ag85B-ESAT-6 adjuvanted with IC31 promotes strong and long-lived Mycobacterium tuberculosis specific T cell responses in naive human volunteers. Vaccine 28(20): 3571-3581.

Van Dissel, J. T., D. Soonawala, et al. (Jan. 20, 2011). Ag85B-ESAT-6 adjuvanted with IC31(R) promotes strong and long-lived Mycobacterium tuberculosis specific T cell responses in volunteers with previous BCG vaccination or tuberculosis infection. Vaccine 29(11): 2100-2109.

Xu, Y., W. Liu, et al. (Aug. 2009). Recombinant Mycobacterium bovis BCG expressing the chimeric protein of antigen 85B and ESAT-6 enhances the Th1 cell-mediated response. Clinical and vaccine immunology : CVI 16(8): 1121-1126.

Yang, X., L. Bao, et al. (Jun. 14, 2011). A novel recombinant Mycobacterium bovis bacillus Calmette-Guerin strain expressing human granulocyte macrophage colony-stimulating factor and Mycobacterium tuberculosis early secretory antigenic target 6 complex augments Th1 immunity. Acta biochimica et biophysica Sinica 43(7): 511-518.

Young, F., J. A. Critchley, et al. (Sep. 14, 2009). A review of co-morbidity between infectious and chronic disease in Sub Saharan Africa: TB and diabetes mellitus, HIV and metabolic syndrome, and the impact of globalization. Globalization and health 5: 9.

Zhang, H., P. Peng, et al. (Jul. 3, 2010). Recombinant Mycobacterium smegmatis expressing an ESAT-6ESAT-6-CFP10 fusion protein induces anti-mycobacterial immune responses and protects against Mycobacterium tuberculosis challenge in mice. Scandinavian journal of immunology 72(4): 349-357.

Zweig, M. H. and G. Campbell (Nov. 2, 1992). Receiver-operating characteristic (ROC) plots: a fundamental evaluation tool in clinical medicine. Clinical chemistry 39(4): 561-577.

Ruhwald, M. and P. Ravn (Aug. 2009). Biomarkers of Latent TB Infection. Expert review of respiratory medicine 3(4): 387-401.

Moon, Hee-Won. and Mina Hur (Apr. 2013). Interferon-gamma Release Assays for the Diagnosis of Latent Tuberculosis Infection: an Updated Review. Annals of clinical and laboratory science 43(2): 221-229.

* cited by examiner

DIAGNOSTIC REAGENTS FOR IMPROVED IN VIVO OR IN VITRO CELL-MEDIATED IMMUNOLOGICAL DIAGNOSIS OF TUBERCULOSIS

The present invention discloses compositions for use as a pharmaceutical or diagnostic reagent for improved in vivo or in vitro cell-mediated immunological diagnosis of tuberculosis in a human or animal. The invention relates to antigen combinations that increases the sensitivity (that gives less false negatives) compared to the existing antigen combinations without compromising the specificity (the amount of false positives). In particular, the invention relates to antigen compositions not including the antigen designated the early secretory antigenic target 6 kDa (ESAT-6) which is currently used in registered products for detecting *Mycobacterium tuberculosis* infection. Alternatively, the novel diagnostic or immunogenic compositions can be used in combination with ESAT-6 to further enhance the sensitivity of cell-mediated diagnosis.

BACKGROUND OF THE INVENTION

Tuberculosis (TB) is a major cause of morbidity and mortality throughout the World. It is estimated that one person develops TB every four seconds and someone will die from the disease every 20-30 seconds. Adding to this, approximately ⅓ of the world's populations is latently infected with *Mycobacterium tuberculosis* (*M. tuberculosis*), the causative agent of TB.

Immunocompetent individuals infected with *M. tuberculosis* in general have a lifetime risk of 10% of developing active TB disease, with this risk increasing dramatically e.g. if the individual is co-infected with HIV (Sonnenberg, 2005) or have diabetes (Young, 2009). If left untreated, each person with active pulmonary TB will infect 10-15 people each year (World Health Organization Tuberculosis Fact Sheet No 104, 2002). Thus, it is important to be able to detect *M. tuberculosis*-infected individuals at an early stage of infection in order to prevent the progression of *M. tuberculosis*-infection to active contagious pulmonary TB. This can be achieved by prophylactic treatment at the earliest time point possible after diagnosis. Therefore, a fast and accurate diagnosis of *M. tuberculosis* infection is an important element of global health measures to control the disease.

Current diagnostic assays to determine *M. tuberculosis* infection include culture, microscopy and PCR of relevant patient material, chest X-rays, the standard tuberculin skin test (TST), and Interferon-gamma release assays (IGRAs). The three first methods are used for diagnosing active contagious TB and are based on the identification of the *M. tuberculosis* bacteria and therefore depend on the presence of bacteria in the sample. This demands a certain bacterial load and access to infectious material and the methods are therefore not suitable for early diagnosis of infection i.e. before the onset of clinical disease. Chest X-ray is insensitive and only applicable for pulmonary TB and for detecting TB in a more progressed stage.

The standard tuberculin skin test, displaying a delayed type hypersensitivity reaction (DTH), is a simple and inexpensive assay based on immunological recognition of mycobacterial antigens in exposed individuals. However, it is far from ideal in detecting *M. tuberculosis* infection. It employs intradermal injection of purified protein derivative (PPD) which is a crude and poorly defined mixture of mycobacterial antigens some of which are shared with proteins from the vaccine sub-strain *M. bovis* bacille Calmette-Guerin (BCG) and from non-tuberculosis environmental mycobacteria. This broad cross-reactivity of PPD causes a poor specificity of TST, leading to a situation where BCG vaccination and exposure to non-tuberculosis mycobacteria gives a test result similar to that seen in *M. tuberculosis*-infected individuals.

*M. tuberculosis* infection mediates a strong cell mediated immune (CMI) response and detection of immune cells and any product deriving from such cells that are generated as a part of the specific response to *M. tuberculosis*-infection would be a suitable method to detect infection (Andersen, 2000). In order to generate such a specific response, the reagent must 1) be broadly recognized by *M. tuberculosis*-infected individuals, and 2) be specific for *M. tuberculosis* thereby discriminating between TB infection, BCG vaccination, and exposure to non-tuberculous environmental mycobacteria.

The genome of *M. tuberculosis* predicts 4018 open reading frames (tuberculist.epfl.ch/, release R27—March 2013). However, only a minority of these are T-cell antigens with a strong and broad recognition by peripheral blood mononuclear cells (PBMCs) from human TB patients. Algorithms to predict T cell epitopes have been developed, but experimental verification was essential to identify the immunodominant antigens CFP10 and ESAT-6. The *M. tuberculosis* extracellular or culture filtrate (CF) proteins constitute a protein fraction enriched in T cell antigens (Andersen 1994) and separation of CF proteins by a two-dimensional proteomics based approach led to identification of 59 human T cell antigens of which 35 had been described before (Deenadayalan, 2010). Although this list may not be exhaustive it emphasizes that only a minor part of the approx. 900 CF proteins (Albrethsen, 2013) are T-cell antigens. Logically one would expect that the most immunodominant antigens encoded from the *M. tuberculosis* genome would be the subset with the highest expression and with current technology it would be possible to rank the genes according to transcription levels under certain growth conditions. However, the contribution that the transcription level makes to the immunogenicity is low and it cannot be used systematically to pinpoint which genes encode relevant antigens (Sidders, 2008).

A highly specific reagent candidate could be sought among antigens from the RD regions (regions of deletion) of the *M. tuberculosis* genome. These regions represent genomic deletions from the *M. bovis* BCG vaccine strain compared to the virulent *M. tuberculosis* strain (Behr, 1999). Therefore, in theory, proteins from these regions (RD proteins) would be excellent candidates as TB diagnostic reagents, i.e. they should not be recognized by healthy un-infected individuals independent of their BCG vaccine status or exposure to non-pathogenic mycobacterial strains. However, of all the predicted genomic ORF's (open reading frames) deleted from BCG it is not known per se which ones are in fact expressed as proteins and furthermore the immunoreactivity remains unknown until tested with sensitized lymphocytes from *M. tuberculosis*-infected individuals. This can e.g. be done in a whole blood assay, by re-stimulation of PBMCs or by injecting the substances into skin similar as PPD/Mantoux test is administered. E.g. evaluation of Rv3872 showed low interferon gamma (IFN-γ) responses in the tested human TB patients (n=7) 1-4 months after diagnosis (WO 99/24577), demonstrating that this RD protein is not frequently recognized, and Rv3872 was therefore not further pursued for a CMI based diagnostic test.

Potential specific *M. tuberculosis* proteins are not limited to RD proteins as e.g. the EspC protein (Rv3615c) is specifically recognized in human TB patients and *M. bovis* infected cattle and not in BCG vaccinated/infected even though the gene is present in BCG (WO2009060184; Sidders, 2008; Millington, 2011). The lack of reaction in BCG-vaccinated individuals is most likely because secretion of Rv3615c is abolished in BCG since it depends on the ESX-1 secretion system which is partly located in the RD1 locus and which is absent in BCG. This antigen is a CMI diagnostic reagent considered as potent as ESAT-6 and CFP10 inducing a comparable strong IFN-γ response (ibid).

When a potentially specific T-cell antigen has been identified, it should be verified that the antigen is specifically recognized in *M. tuberculosis* infected individuals and not in BCG vaccinated persons. For Rv3873 from RD1 it appeared that the protein was a member of a protein family with a conserved motif in amino acids 118-135 also present in other *M. tuberculosis* proteins. As a broadly recognized T-cell epitope was present in this motif, BCG vaccinated individuals also responded to the peptide spanning this sequence (Liu, 2004). However, cross-reactivity was also observed to Rv3878 and Rv3879c although no homology was detected by comparing with sequences of other known mycobacterial proteins (Liu, 2004) emphasizing that the specificity of a potential diagnostic candidate needs to be experimentally verified. In the same manner, Rv2653c from RD13 was recognized both in BCG vaccinated donors and TB patients although database searches with the BLAST algorithm did not reveal any obvious mycobacterial protein which could explain the observed cross-reactivity (Aagaard, 2004).

Having identified *M. tuberculosis* specific proteins with potential for diagnosis of *M. tuberculosis* infection by CMI based assay it remains to be investigated if a pool of such proteins/peptides will provide the desired sensitivity for a diagnostic test. It is not possible to predict how much a given antigen will add to the sensitivity after combination to already defined diagnostic antigens; this has to be experimentally evaluated for each antigen, and preferably in TB patients from different parts of the World with different genetic backgrounds.

The diagnostic potential of CFP10 (Rv3874), ESAT-6 (Rv 3875), two low molecular proteins from the RD1 region, and TB7.7 (Rv2654) is very well documented (Brock, 2004; Moon, 2013, WO2004099771) and are currently used in different diagnostic reagents registered for human use. Peptides covering CFP10 and ESAT-6 are used in the T-SPOT®.TB test, which is a cellular blood test that detects the immune response of T cells found in PBMCs that have been re-stimulated with ESAT-6 and CFP10. This response is detected by a highly sensitive enzyme-linked immunospot methodology, designated ELISPOT, and is commercialized as the T-SPOT.TB test. This test is highly sensitive and independent of BCG vaccination status. Another registered test for detection of *M. tuberculosis*-infection is QuantiFERON®-TB Gold, which is an in-vitro diagnostic technology enabling detecting of immune responses in whole blood samples upon re-stimulation with peptides covering ESAT-6, CFP10 and a single peptide from TB7.7. Both of these tests measure the production of interferon-gamma (IFN-γ) in response to exposure with the selected specific antigen peptide pools and are at present considered state-of-the-art. T-SPOT.TB and QuantiFERON®-TB Gold test are collectively recognized as IFN-γ release assays (IGRAs).

Other cytokines and chemokines than IFN-γ have also shown relevance when monitoring the immunological response to mycobacterial antigens. IFN-γ-induced protein (IP-10) is expressed at 100-fold higher levels compared to IFN-γ and diagnostic assays based on the secretion of IP-10 have shown diagnostic performance comparable to IFN-γ release assays (Ruhwald, 2009).

In addition to these in vitro tests, which are already registered for human use and used throughout the world, ESAT-6 and CFP10 have also proven to be effective as skin-test reagents. Clinical studies have shown that a skin test applied in the same way as PPD but using ESAT-6 and CFP10 produced and delivered as recombinant proteins can be used to diagnose *M. tuberculosis* infection and is unaffected by the BCG vaccination status (Aggerbeck, 2013).

Despite the widespread use of BCG and several diagnostic methods including IGRA, TB keeps taking its toll with almost two million deaths a year and there is a continued need to develop immunodiagnostic tests with improved sensitivity. Immunocompromised patients are at higher risk of developing TB and unfortunately both TST and IGRAs in their present form, performs suboptimal in these groups. The patient groups in highest need of improved testing comprise: HIV-infected patients, patients with immune mediated inflammatory diseases, patients receiving immune suppressive medication (e.g. prednisolone or TNF-α inhibitors) and patients with chronic renal failure. In e.g. HIV infected it is well known that a low CD4 cell count (e.g. <250 cells/pi) is strongly associated with higher rates of indeterminate test outcome, compromised test sensitivity for active TB and decreased likelihood for positive test response in exposed individuals reviewed in (Redelman-Sidi, 2013).

Another very relevant group for targeted testing is children. The diagnosis of latent TB infection (LTBI) and TB in children is difficult, microbiological confirmation of infection is often not obtained and treatment is directed by the clinical presentation alone. In both active and presumed latently infected young children, the immune system is immature, and is the likely cause of lower cytokine release and compromised IGRA performance. Recently it was shown that the QuantiFERON©-TB Gold test had a sensitivity of 53% in 81 children with microbiologically confirmed TB, underpinning the need for improved immunodiagnostic tests for *M. tuberculosis* infection in children (Schopfer, 2013).

The core problem with the IGRA test performance in the high-risk patient groups mentioned above (e.g. Immunosuppressed, HIV infected, Children) is that the underlying immunosuppressive condition that drives the increased risk of TB disease in itself is characterized by low CMI responses and low IFN-γ release in response to antigens. As the IGRA result is determined based on comparison of the magnitude of IFN-γ release to a cut off, a compromised IFN-γ release increases the risk of the test result becoming false negative. Therefore, it is obvious to the skilled addressee that including more specific antigens will recruit more specific T cells and result in an augmented CMI response and release of IFN-γ and consequently lowering the risk of the response falling below the cut off. Therefore adding additional specific antigens addresses a major limitation in the IGRA tests by improving diagnostic sensitivity.

Another benefit from diagnosing infection of *M. tuberculosis* based on responses of higher magnitude is an increased analytical accuracy and more reliable test results. In the QuantiFERON®-TB Gold test the cut off for positive test is 0.35 IU/ml or 17.5 pg/ml, a very low concentration which is difficult to determine with high precision—even with sensitive methods as ELISA. For example, the largest precision study of an IGRA to date, found considerable variability in TB response measured by QuantiFERON-TB Gold In-Tube on retesting of the same patient sample. Variability within individuals included differences up to 0.24 IU/ml, in either direction, when the initial response was between 0.25 and 0.80 IU/ml. This led to the conclusion that positive QuantiFERON TB Gold In-Tube test results less than 0.59 IU/ml should be interpreted cautiously (Metcalfe AJRCCM 2012).

Modelling studies suggest that without new vaccines, TB cannot be eliminated and novel and more effective vaccines are an international priority. The overall idea is to supplement the current BCG vaccine with a booster subunit vaccine or creating a novel live TB vaccine to replace BCG. There are an increasing number of experimental vaccines in clinical development and the emerging consensus is that ESAT-6 appears to be an essential vaccine antigen. Thus, many of the novel vaccines currently at the preclinical level or in clinical testing contain ESAT-6. Recently, Aeras Foundation announced the first-in-man trial of an ESAT-6-containing vaccine designed to protect people already latently infected with TB, from developing active TB disease (Aagaard, 2011). Several live vaccine candidates are also directly recombinantly engineered to express ESAT-6 e.g. rBCG:GE (Yang, 2011), rM.S-e6c10 (Zhang, 2010), Salmonella/Ag85B-ESAT-6 (Hall, 2009), rBCG-A(N)-E-A(C) (Xu, 2009) or fusion proteins incorporating ESAT-6 e.g. H1 (van Dissel, 2010; van Dissel, 2011). Unfortunately, the use of ESAT-6 based diagnostics in the IGRA test and vaccination with an ESAT-6 containing vaccine is an exact repetition of the cross-reaction problem associated with the parallel use of TST and BCG.

Consequently, there is a great need for a specific diagnostic reagent that can be used in parallel with both BCG and ESAT-6 containing vaccines. Using in vivo or in vitro assays the reagent should be able to detect *M. tuberculosis* infections in humans and animals and to discriminate not only between TB infection and vaccination with BCG or the novel ESAT-6 containing vaccines but also exposure to non-pathogenic environmental mycobacteria. The diagnostic reagent should have at least the same sensitivity as the current combination of ESAT-6, CFP10 and in some diagnostic assays TB7.7.

EP2417456 describes such a system where using Rv3615c in conjunction with CFP-10 provides diagnostic sensitivity very similar to the ESAT-6/CFP-10 combination.

Because of the unique characteristics of ESAT-6 being highly immunogenic and specific for *M. tuberculosis*-infection, it is not likely that replacing ESAT-6 with a single antigen will increase sensitivity compared to ESAT when studying various population groups. This has e.g. be demonstrated by Brock et al. showing recognition of single antigens between 14-43% in TB patients compared to ESAT-6 giving rise to a response in 75% in same patient group. Given that the majority of antigens are less immunogenic compared to ESAT-6, it is more likely that a pool of antigens is needed for responses of high magnitude and improved diagnostic sensitivity.

As exemplified it is not simple to predict the sensitivity and specificity of antigens combinations; rather this requires a detailed design of specific antigen combinations. Adding to this, by increasing the number of peptides in the diagnostic pool it introduces the risk of decreasing the specificity further by increasing the numbers of false positives emphasizing that the diagnostic or immunogenic compositions for specific diagnosis of TB needs to be carefully selected and tested.

There is therefore an urgent need for improved in vivo or in vitro cell-mediated immunological diagnosis of infection with *M. tuberculosis* in a human or animal. That is a need for antigen combinations that increases the sensitivity (that gives less false negatives) compared to the existing antigen combinations without compromising the specificity (amount of false positives). The needed improved antigen combinations relates to both antigen compositions not including the ESAT-6 antigen to anticipate the situation when a ESAT-6 comprising vaccine is introduced, and antigen combinations comprising ESAT-6 to improve the present state-of-the-art diagnostic reagents.

Our data demonstrate that the CFP10/ESAT6 and the CFP10/Rv3615c combinations can be further improved by adding peptides derived from three novel antigens with diagnostic potential. This novel finding is unexpected for two reasons:
 a) The majority (>99%) of the antigens on the TB genome are non-specific and shared among various mycobacterial species so identifying strongly recognized antigens that are specific for *Mycobacterium tuberculosis* has been very difficult
 b) The sensitivity of the CFP10/RV3615c and CFP10/ESAT6 diagnostic combination are already very high so increasing the sensitivity even further becomes increasingly difficult due to non-specific responses.

The present invention is therefore very encouraging as it describes peptides with the ability not only to increase sensitivity of the CFP10/RV3615c combination but also of the current diagnostic cocktail that includes ESAT6—and without compromising specificity.

SUMMARY OF THE INVENTION

The invention is related to improved detection of infections caused by species of the TB complex (*M. tuberculosis, M. bovis, M. africanum*) and discriminate between TB infection and vaccination. The improved diagnostic composition must not interfere with the effect of antigens from neither 1) a novel ESAT-6 containing TB vaccine, 2) BCG nor 3) exposure to non-pathogenic environmental mycobacteria. The invention discloses improved diagnostic or immunogenic compositions, which can be used either in vivo or in vitro to detect a cellular response to *M. tuberculosis* infection and thereby be used for diagnosing TB. By using a cocktail or pool of antigens or cocktail or pool of peptides covering these antigens we have made the test highly sensitive despite the absence of ESAT-6 in the diagnostic immunogenic compositions. In addition, we have further improved the ESAT-6 comprising diagnostic immunogenic compositions used at present.

DETAILED DISCLOSURE OF THE INVENTION

This diagnostic method is based on cellular mediated immunological (CMI) recognition of antigens expressed by the *M. tuberculosis* (or other mycobacteria from the tuberculosis complex) bacteria during infection. Therefore, the test does not require presence of the bacteria as traditional culture, microscopy and PCR methods. This means that the test can be applied early in the infection phase and that the test is applicable regardless of the anatomical site of infection. The method is ideal in contact tracing as replacement for the currently used TST.

By selecting *M. tuberculosis*-specific antigens with theoretical diagnostic potential and testing the recognition in a series of human TB patients, we were able to identify three diagnostic pools that 1) is lacking ESAT-6 and thereby can be used also in ESAT-6 vaccinated individuals to discriminate between *M. tuberculosis*-infection and vaccination, 2) showed the same high specificity as ESAT-6 containing diagnostic pools, and 3) exhibited a sensitivity for *M. tuberculosis*-infection superior to that obtained by a combination of ESAT-6, CFP10, and TB7.7.

The present invention discloses a diagnostic or immunogenic composition comprising a mixture of substantially pure polypeptides comprised of amino acid sequences selected from:

a)
Rv3874 (SEQ ID NO1), Rv3615c (SEQ ID NO 2) and additional compositions selected from Rv3865 (SEQ ID NO 3), Rv2348c (SEQ ID NO 4), Rv3614 (SEQ ID NO 5), Rv2654 (SEQ ID NO 6) and Rv3877 (SEQ ID NO 7);
or b)
a mixture of fragments of said polypeptides;
or c)
where the selected mixture of polypeptides or fragments of said polypeptides have at least 80% sequence identity to any of the polypeptides from the selection in a) or b) and at the same time being immunogenic.

Under circumstances where ESAT-6-containing vaccines will not be registered for human use, in areas where ESAT-6-containing vaccines are not being used and under other circumstances e.g. for further increasing the sensitivity of a diagnostic test, any of the above disclosed diagnostic or immunogenic compositions can be supplemented with ESAT-6 (SEQ ID NO 51) or one or more fragments thereof.

A preferred diagnostic composition comprises a mixture of fragments comprising the immunogenic epitopes of Rv3874, Rv3615c and optionally ESAT-6 wherein the fragments comprising immunogenic epitopes of SEQ ID NO 1 is chosen from SEQ ID NO 9-14 and the fragments comprising immunogenic epitopes of SEQ ID NO 2 is chosen from SEQ ID NO 15-18 or SEQ ID NO 59-63 and the fragments comprising immunogenic epitopes of SEQ ID NO 51 is chosen from SEQ ID NO 52-58, wherein the fragments comprising immunogenic epitopes of SEQ ID NO 3 is chosen from SEQ ID NO 19-21 and the fragments comprising immunogenic epitopes of SEQ ID NO 4 is chosen from SEQ ID NO 22-25 and the fragments comprising immunogenic epitopes of SEQ ID NO 5 is chosen from SEQ ID NO 26-45 and wherein the fragments comprising immunogenic epitopes of SEQ ID NO 6 is SEQ ID NO 8 and the fragments comprising immunogenic epitopes of SEQ ID NO 7 is chosen from SEQ ID NO 46-50.

The polypeptides in the diagnostic or immunogenic composition can be present as separate entities or where some or all of the polypeptides are fused together optionally via linkers or spacers.

A preferred diagnostic or immunogenic composition comprises a pool or mixture of SEQ ID NO 9-14, SEQ ID NO 15-18, SEQ ID NO 19-21 and SEQ ID NO 22-25 mentioned in the examples as peptide pool A.

Detailed Description of the Preferred Polypeptides and Fragments of Said Polypeptides:

CFP10 (SEQ ID NO 1) is a major ESX-1 protein. The following 6 peptides covering the entire amino acid sequence of CFP10 were selected (SEQ IDs no 9-14)

Rv3615c (SEQ ID NO 2) is a protein secreted by the ESX-1 system. 4 peptides covering amino acids 55-103 were selected (SEQ ID NO 15-18). Alternative peptides covering the C-terminal part of Rv3615c are the five peptides with the amino acid sequence SEQ ID NO 59-63.

Rv3865 (SEQ ID NO 3) is a ESX-1 secretion-associated protein: 3 peptides covering amino acids 9-44 were selected (SEQ IDs no 19-21)

Rv2348c (SEQ ID NO 4) is located in the RD7 region which has been shown to be absent in BCG: 4 peptides covering amino acids 56-109 of the full length protein sequence were selected (SEQ IDs no 22-25)

Rv3614c (SEQ ID NO 5) is a secreted protein: 20 peptides covering the entire sequence were selected (SEQ IDs no 26-45)

Rv2654c (SEQ ID NO 6)) is a protein with unknown function encoded by the RD11 region: peptide 4 was selected (SEQ ID no 8)

Rv3877 (SEQ ID NO7) is located in the RD1 region and is not present in BCG: 5 peptides covering amino acid 220-284 in the full length protein (511 aa) were selected (SEQ IDs no 46-50)

ESAT-6 (Rv3875; SEQ ID NO 51) is a major ESX-1 protein. 7 peptides covering the entire sequence was selected (SEQ ID NO 52-58)

The invention further discloses the use of the diagnostic or immunogenic compositions for the preparation of a pharmaceutical composition for diagnosis of TB caused by virulent mycobacteria, e.g. by *M. tuberculosis, Mycobacterium bovis*, or *Mycobacterium africanum* and a CMI diagnostic tool or kit comprising a diagnostic or immunogenic composition mentioned above for in vitro or in vivo diagnosis of TB.

The invention also discloses in vitro and in vivo methods of diagnosing TB caused by virulent mycobacteria, e.g. by *M. tuberculosis, Mycobacterium africanum* or *Mycobacterium bovis*, in an animal, including a human being, using above mentioned diagnostic or immunogenic compositions.

The in vivo method of diagnosing TB comprises intradermally injecting, in the animal including a human being, a pharmaceutical composition as defined above where a positive skin response at the location of injection being indicative of the animal having TB, and a negative skin response at the location of injection being indicative of the animal not having TB.

The in vitro method of diagnosing TB comprising contacting a sample, e.g. a blood sample, with a diagnostic or immunogenic composition according to the invention in order to detect a positive reaction, e.g. proliferation of the cells or release of cytokines such as IFN-γ.

The present diagnostic or immunogenic compositions can replace compositions currently being used in established IGRA tests (CFP10/Rv3874 and ESAT-6/Rv3875 in TB.SPOT®.TB test and TB7.7/Rv2654c, CFP10/Rv3874 and ESAT-6/Rv3875 in QuantiFERON®-TB Gold.

The method furthermore holds the following improvement compared to CFP10/Rv3874 and ESAT-6/Rv3875 in TB.SPOT®.TB test and TB7.7/Rv2654c, CFP10/Rv3874 and ESAT-6/Rv3875 in QuantiFERON®-TB Gold:

If an individual has been vaccinated with an ESAT-6 containing vaccine, such as a subunit protein vaccine comprising ESAT-6 or a recombinant live vaccine engineered to or inherently expressing ESAT-6, the composition avoids the use of ESAT-6 and is consequently still specific for *M. tuberculosis*-infection. This is not the case for CFP10 and ESAT-6 in TB.SPOT®.TB test and TB7.7, CFP10 and ESAT-6 in QuantiFERON®-TB Gold or any other test based on ESAT-6.

ESAT-6 containing compositions are being used in CMI-based *M. tuberculosis* tests. The test presented can avoid the use of ESAT-6 and takes advantage of a broad recognition obtained from using more than one *M. tuberculosis*-specific antigen. In our test we obtain with the combination of CFP10, Rv3615c, Rv3865, and Rv2348c (peptide pool A) a sensitivity of 87% and a specificity of 98% compared to a sensitivity of 74% and specificity of 96% using the Quantiferon antigens. Thus, despite the lack of ESAT-6, known to be a highly sensitive antigen and recognized by a high proportion of individuals harboring a *M. tuberculosis*-infection, the compositions tested herein obtain >10% higher sensitivity rate compared to the well-known compositions based on ESAT-6 and currently used in IGRA assays.

Herein, we also present data showing that by adding ESAT-6 to the peptide pool consisting of CFP10, Rv3615c, Rv3865, and Rv2348c we can further improve the diagnostic performance. By adding ESAT-6 to the specified peptide pool we can increase the magnitude of responses which could be relevant for diagnosis in individuals with different immunosuppressive complications e.g. HIV or for use in e.g. children. Also, by using a combination of peptides from all five antigens (CFP10, ESAT-6, Rv3865, Rv2348c, and Rv3615c) we could increase the frequency of patients with a confirmed TB diagnosis with 3% compared to having the pool of CFP10, Rv3615c, Rv2348c and Rv3865 alone.

The present invention also discloses in vivo testing for diagnosis of TB. This could be in the format of a skin test on an animal, including a human being, with the compositions mentioned above. The skin test being: intradermally injecting in an animal or applying on the animals skin, e.g. with a patch or bandage, a composition of the present invention. A positive skin test response at the site of injection or application being indicative of the animal or human having TB, and a negative skin response at the location of injection or application being indicative of the animal not having TB.

It is not necessary that the peptide pools of the invention comprises the proteins in their full length, as a sequence of only 6-9 amino acids (T-cell epitope) is sufficient for eliciting an immune response but full length proteins will also be useful. As it is possible for a skilled person to determine the exact and minimal amino acid sequence for the T-cell epitope embedded in a protein, the present invention also relates to fragments (immunogenic portions) of polypeptides comprising said T-cell epitopes (or analogues thereto) without the specific additional amino acids as full length proteins and fusion proteins comprising said T-cell epitopes (optionally coupled via linker or spacer), and to cocktails or pools comprising such polypeptides or fusion proteins.

Further embodiments of the invention are described in the examples and in the claims.

Definitions

Polypeptides

The word "polypeptide" in the present invention should have its usual meaning. That is an amino acid chain of any length, including a full-length protein, oligopeptides, short peptides and fragments thereof, wherein the amino acid residues are linked by covalent peptide bonds. The polypeptide may be chemically modified by being glycosylated, by being lipi-dated e.g. by chemical lipidation with palmitoyloxy succinimide as described by Mowat et al (Mowat, 1991) or with dodecanoyl chloride as described by (Lustig, 1976), by comprising prosthetic groups, or by containing additional amino acids such as e.g. a his-tag or a signal peptide.

Each polypeptide may thus be characterized by specific amino acids and be encoded by specific nucleic acid sequences. It will be understood that such sequences include analogues and variants produced by recombinant or synthetic methods wherein such polypeptide sequences have been modified by substitution, insertion, addition or deletion of one or more amino acid residues in the recombinant polypeptide and still be immunogenic in any of the biological assays described herein. Substitutions are preferably "conservative". These are defined according to the following table. Amino acids in the same block in the second column and preferably in the same line in the third column may be substituted for each other. The amino acids in the third column are indicated in one-letter code.

| | | |
|---|---|---|
| ALIPHATIC | Non-polar | GAP |
| | | ILV |
| | Polar-uncharged | CSTM |
| | | NQ |
| | Polar-charged | DE |
| | | KR |
| AROMATIC | | HFWY |

A preferred polypeptide within the present invention is a fragment of an immunogenic antigen from *M. tuberculosis*. Such antigen can for example be derived from the *M. tuberculosis* cell and/or *M. tuberculosis* culture filtrate. Thus, a polypeptide comprising an immunogenic portion of one of the above antigens may consist entirely of the immunogenic portion, or may contain additional sequences. The additional sequences may be derived from the native *M. tuberculosis* antigen or be heterologous and such sequences may, but need not, be immunogenic.

In the present context the term "substantially pure polypeptide fragment" means a polypeptide preparation which contains at most 10% by weight of other polypeptide material with which it is natively associated (lower percentages of other polypeptide material are preferred, e.g. at most 4%, at most 3%, at most 2% and at most 1). It is preferred that the substantially pure polypeptide is at least 96% pure, i.e. that the polypeptide constitutes at least 96% by weight of total polypeptide material present in the preparation, and higher percentages are preferred, such as at least 97%, at least 98%, at least 99%, at least 99.25%, at least 99.5%, and at least 99.75%. It is especially preferred that the polypeptide fragment is in "essentially pure form", i.e. that the polypeptide fragment is essentially free of any other antigen with which it is natively associated, i.e. free of any other antigen from bacteria belonging to the tuberculosis complex or a virulent *mycobacterium*. This can be accomplished by preparing the polypeptide fragment by means of recombinant methods in a non-mycobacterial host cell as will be described in detail below, or by synthesizing the polypeptide fragment by the well-known methods of solid or liquid phase peptide synthesis, e.g. by the method described by (Merrifield 1963) or variations thereof.

By "tuberculosis" (TB) is understood an infection caused by a virulent *mycobacterium* from the tuberculosis complex, capable of causing the TB infection and disease in an animal or in a human being. Examples of virulent mycobacteria are *M. tuberculosis, M. africanum* and *M. bovis*. Examples of relevant animals are cattle, possums, badgers and kangaroos.

By "a TB patient" is understood an individual with culture or microscopically proven infection with virulent mycobacteria, and/or an individual clinically diagnosed with TB and who is responsive to anti-TB chemotherapy. Culture, microscopy and clinical diagnosis of TB are well known by any person skilled in the art.

By the term "delayed type hypersensitivity reaction" (DTH) is understood a T-cell mediated inflammatory response elicited after the injection of a polypeptide into, or application to, the skin, said inflammatory response appearing 72-96 hours after the polypeptide injection or application.

By the term "cytokine" is understood any immunomodulating agent such as interleukins and interferons that can be used as an indication of an immunological response. This includes e.g. interferon-gamma "IFN-γ", interferon-gamma inducible protein 10, also known as CXCL10 or "IP-10", and interleukin 2 (IL-2).

Throughout this specification, unless the context requires otherwise, the word "comprise", or variations thereof such as "comprises" or "comprising", will be understood to imply the inclusion of a stated element or integer or group of elements or integers but not the exclusion of any other element or integer or group of elements or integers.

Sequence Identity

The term "sequence identity" indicates a quantitative measure of the degree of homology between two amino acid sequences of equal length or between two nucleotide sequences of equal length. The two sequences to be compared must be aligned to best possible fit possible with the insertion of gaps or alternatively, truncation at the ends of the protein sequences. The sequence identity can be calculated as $$\frac{(N_{ref} - N_{dif})100}{N_{ref}},$$

wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC ($N_{dif}=2$ and $N_{ref}=8$). A gap is counted as non-identity of the specific residue(s), i.e. the DNA sequence AGTGTC will have a sequence identity of 75% with the DNA sequence AGTCAGTC ($N_{dif}=2$ and $N_{ref}=8$). Sequence identity can alternatively be calculated by the BLAST program e.g. the BLASTP program (Pearson, 1988) (www.ncbi.nlm.nih.gov/cgi-bin/BLAST). In one aspect of the invention, alignment is performed with the sequence alignment method ClustalW with default parameters as described by Thompson, et al (Thompson, 1994), available at www2.ebi.ac.uk/clustalw/.

A preferred minimum percentage of sequence identity is at least 80%, such as at least 85%, at least 90%, at least 91%, at least 92%, at least 93%, at least 94%, at least 95%, at least 96%, at least 97%, at least 98%, at least 99%, and at least 99.5%.

Immunogenic Epitope

An immunogenic epitope of a polypeptide is a part of the polypeptide, which elicits an immune response in an animal or a human being, and/or in a biological sample determined by any of the biological assays described herein. The immunogenic epitope of a polypeptide may be a T-cell epitope or a B-cell epitope. Immunogenic epitope can be related to one or a few relatively small parts of the polypeptide, they can be scattered throughout the polypeptide sequence or be situated in specific parts of the polypeptide. For a few polypeptides epitopes have even been demonstrated to be scattered throughout the polypeptide covering the full sequence (Ravn, 1999).

In order to identify relevant T-cell epitopes which are recognised during an immune response, it is possible to use a "brute force" method: Since T-cell epitopes are linear, deletion mutants of the polypeptide will, if constructed systematically, reveal what regions of the polypeptide are essential in immune recognition, e.g. by subjecting these deletion mutants e.g. to the IFN-γ assay described herein. Another method utilises overlapping peptides for the detection of MHC class II epitopes, preferably synthetic, having a length of e.g. 20 amino acid residues derived from the polypeptide. These peptides can be tested in biological assays (e.g. the IFN-γ assay as described herein) and some of these will give a positive response (and thereby be immunogenic) as evidence for the presence of a T cell epitope in the peptide. For the detection of MHC class I epitopes it is possible to predict peptides that will bind (Stryhn, 1996) and hereafter produce these peptides synthetic and test them in relevant biological assays e.g. the IFN-γ assay as described herein. The peptides preferably having a length of e.g. 8 to 11 amino acid residues derived from the polypeptide.

Although the minimum length of a T-cell epitope has been shown to be at least 6 amino acids, it is normal that such epitopes are constituted of longer stretches of amino acids. Hence, it is preferred that the polypeptide fragment of the invention has a length of at least 7 amino acid residues, such as at least 8, at least 9, at least 10, at least 12, at least 14, at least 16, at least 18, at least 20, at least 22, at least 24, and at least 30 amino acid residues. Hence, in important embodiments of the inventive method, it is preferred that the polypeptide fragment has a length of at most 50 amino acid residues, such as at most 40, 35, 30, 25, and 20 amino acid residues. It is expected that the peptides having a length of between 10 and 30 amino acid residues will prove to be most efficient as MHC class II epitopes and therefore especially preferred lengths of the polypeptide fragment used in the inventive method are 18, such as 15, 14, 13, 12 and even 11 amino acid residues. It is expected that the peptides having a length of between 7 and 12 amino acid residues will prove to be most efficient as MHC class I epitopes and therefore especially preferred lengths of the polypeptide fragment used in the inventive method are 11, such as 10, 9, 8 and even 7 amino acid residues.

Immunogenic portions (fragments comprising immunogenic epitopes) of polypeptides, comprising the immunogenic epitope, may be recognised by a broad part (high frequency) or by a minor part (low frequency) of the genetically heterogenic human population. In addition some immunogenic portions induce high immunological responses (dominant), whereas others induce lower, but still significant, responses (subdominant). High frequency><low frequency can be related to the immunogenic portion binding to widely distributed MHC molecules (HLA type) or even by multiple MHC molecules (Sinigaglia, 1988; Kilgus, 1991). Fragments comprising immunogenic epitopes from said polypeptides can be present as overlapping peptides of at least 10 amino acid length thereby spanning several epitopes.

Variants

A common feature of the polypeptides of the compositions of the invention is their capability to induce an immunological response as illustrated in the examples. It is understood that a variant of a polypeptide of the invention produced by substitution, insertion, addition or deletion is also immunogenic determined by any of the assays described herein.

Immune Individual

An immune individual is defined as a person or an animal, which has cleared or controlled an infection with virulent mycobacteria or has received a vaccination with *M. bovis* B Immunogenic An immunogenic polypeptide is defined as a polypeptide that induces an immune response in a biological sample or an individual currently or previously infected with a virulent *mycobacterium*. An immunogenic polypeptide is synonymous for an antigen or an antigenic polypeptide and the two terms imunogen and antigen are used indiscriminately in this disclosure; the strict definition for an antigen is that it is able to bind specifically to a T or B cell receptor and the strict definition for an immunogen is that it is able to provoke an immune response, but when it comes to diagnosis the effect of the two terms are the same and hence used indiscriminately here.

CMI Diagnosis

The immune response may be monitored by one of the following methods: An in vitro CMI response is determined by release of a relevant cytokine such as IFN-γ, from lymphocytes withdrawn from an animal or human being currently or previously infected with virulent mycobacteria, or by detection of proliferation of these T cells. The induction being performed by the addition of the immunogenic composition to a suspension of blood cells comprising preferably from $1 \times 10^5$ cells to $1 \times 10^6$ cells per well. The cells being isolated from either the blood, the spleen, the liver or the lung and the addition of the immunogenic composition resulting in a concentration of for example 1-200 μg per ml suspension and the stimulation being performed from two to five days. For monitoring cell proliferation the cells are pulsed with radioactive labeled Thymidine and after 16-22 hours of incubation detecting the proliferation by liquid scintillation counting or any other methods to detect a proliferative response. The release of IFN-γ can be determined by the ELISA method, which is well known to a person skilled in the art. Other cytokines and chemokines than IFN-γ could be relevant when monitoring the immunological response to the polypeptide, such as IL-2, IL-12, TNF-α, IL-4, TGF-β, IP-10, MIP-1β, MCP-1, IL-1RA and MIG. Another and more sensitive method for determining the presence of a cytokine (e.g. IFN-γ) is the ELISPOT method where the cells isolated from e.g. the blood are diluted to a concentration of preferably of 1 to $4 \times 10^6$ cells/ml and incubated for 18-22 hrs in the presence of the diagnostic or immunogenic composition resulting in a concentration of preferably 1-200 jag per ml. The cell suspensions are hereafter diluted to 1 to $2 \times 10^6$/ml and transferred to polyvinylidene fluoride membrane microtiter plates coated with anti-IFN-γ and incubated for preferably 4 to 16 hours. The IFN-γ producing cells are determined by the use of labeled secondary anti-IFN-γ antibody and a relevant substrate giving rise to spots, which can be enumerated using a dissection microscope. The FluoroSpot assay is a modification of the ELISPOT assay and is based on using multiple fluorescent anticytokines which makes it possible to spot two cytokines in the same assay potentially allowing for improved prediction of risk of disease as described below for IL-2 and IFN-γ co-determination. It is also possible to determine the presence of a cytokine or chemokine response using lateral flow technology. This type of assay—well known from rapid pregnancy tests—enables rapid detection of the level of cytokine or chemokine released and enables diagnosis of infection and disease also in very resource restraint settings. Other immunoassays including colorimetric assays such as turbidimetry are well known to the skilled person and can be used for high throughput detection of cytokine or chemokine levels. It is also a possibility to determine the presence of mRNA coding for the relevant cytokine by the use of the polymerase chain reaction (PCR) technique. Detection of the cytokine or chemokine at mRNA level is usually faster than at the protein level as mRNA transcription precedes protein synthesis. For example mRNA levels of the cytokine IFN-γ and the chemokine IP-10 are optimal at shorter incubation periods compared to protein level. Cytokine and chemokine signals detected at mRNA level can be done as early as 2 hours after stimulation, and maximum levels are reached at 6-10 hours. Usually one or more cytokines will be measured utilizing for example the PCR, Lateral Flow, ELISPOT or ELISA. It will be appreciated by a person skilled in the art that a significant increase or decrease in the amount of any of these cytokines induced by a specific polypeptide can be used in evaluation of the immunological activity of the polypeptide. Also, the skilled addressee appreciates that certain patterns of cytokine release are associated with certain clinical states. In particular a dominance of IFN-γ to IL-2 has been suggested as indicative of incipient active TB disease, whereas IL-2 dominance to IFN-γ suggests infection control and low risk of developing TB disease despite of the presence of infection in the mammal subjected for testing (Biselli, 2010; Sester, 2011).

In vitro CMI response can be augmented by the addition of cytokines such as IL-7 and/or IL-15, also augmented release can be done by blocking inhibitory substances such as IL-10, IL-4, IL-5 and/or IL-13. Similar CMI responses can be more reliably detected if the in vitro culture conditions are optimal for the cells undergoing stimulation. Such conditions can be brought forward by addition of nutrients e.g. in the form of simple and complex sugars.

A simpler and yet sensitive method is the use of whole blood samples without prior isolation of mononuclear cells. With this method a sample of heparinized whole blood (with or without prior lysis of the erythrocytes) in an amount of 50-1000 ml and incubation being performed in 18 hours to 6 days with the diagnostic or immunogenic composition of the invention resulting in a concentration of preferably 1-200 μg/ml suspension. The supernatant is harvested and the release of IFN-γ (or any other relevant released cytokine e.g. IP-10, IL-2 or others) can be determined by the ELISA method, which is well known to a person skilled in the art.

Another also simple and yet sensitive in vitro method to determine a CMI response is by spotting the sample—after incubation with the diagnostic or immunogenic composition—on filter paper e.g. Whatman 903 or Whatman FTA paper. After drying, the spotted sample is stabilized and cytokine and chemokine levels in the sample can be detected at a later stage. CMI responses are readily detected with the above mentioned techniques for protein or mRNA measurements. This method is particularly suitable for low resource settings or for high throughput sample preparation and analysis.

Another in vitro method comprises vacutainer blood collection tubes precoated with the immunogenic polypeptides or fusion proteins hereof optionally also added a blood stabilizer such as Heparin and/or nutrients. Precoated incubation tubes allow for simple blood collection and eliminate the risk of exposure to blood borne infection while preparing the sample for in vitro incubation. Such vacutainer tubes are ideal for high throughput processing and automation.

The invention therefore also relates to an in vitro method for diagnosing ongoing or previous sensitisation in an animal or a human being with a virulent *mycobacterium*, the method comprising providing a blood sample from the animal or human being, and contacting the sample from the animal with the polypeptide or the composition of the invention, a significant release into the extracellular phase of at least one cytokine by mononuclear cells in the blood sample being indicative of the animal being sensitised. A positive response being a response more than release from a blood sample derived from a patient without the TB diagnosis plus two standard deviations.

An in vitro CMI response may also be determined by the use of T cell lines derived from an immune individual or an *M. tuberculosis* infected person where the T cell lines have been driven with either live mycobacteria, extracts from the bacterial cell or culture filtrate for 10 to 20 days with the addition of IL-2. The induction being performed by addition of preferably 1-200 jag polypeptide per ml suspension to the T cell lines containing for example $1\times10^5$ cells to $3\times10^5$ cells per well and incubation being performed from two to six days. The induction of IFN-γ or release of another relevant cytokine is detected by ELISA. The stimulation of T cells can also be monitored by detecting cell proliferation using radioactively labeled Thymidine as described above. For both assays a positive response being a response more than background plus two standard deviations.

An in vivo CMI response (e.g. skin-test, transdermal skin-test, patch skin test) which may be determined as a positive DTH response after intradermal injection or local application patch of at preferably 1-200 μg of each polypeptide in the diagnostic or immunogenic composition of the invention to an individual who is clinically or subclinically infected with a virulent *mycobacterium*, a positive response having a diameter of at least 5 mm 72-96 hours after the injection or application.

Diagnostic Accuracy and Cut-Offs

The sensitivity of any given diagnostic test define the proportion of individuals with a positive response who are correctly identified or diagnosed by the test, e.g. the sensitivity is 100%, if all individuals with a given condition have a positive test. The specificity of a given screening test reflects the proportion of individuals without the condition who are correctly identified or diagnosed by the test, e.g. 100% specificity is, if all individuals without the condition have a negative test result.

Sensitivity is defined as the proportion of individuals with a given condition (e.g. active TB infection), who are correctly identified by the described methods of the invention (e.g. has a positive IFN-γ test result).

Specificity herein is defined as the proportion of individuals without the condition (e.g. no exposure to active TB infection), who are correctly identified by the described methods of the invention (e.g. has a negative IFN-γ test result).

Receiver-Operating Characteristics

Accuracy of a diagnostic test is best described by its receiver-operating characteristics (ROC) (Zweig, 1993). The ROC graph is a plot of all of the sensitivity/specificity pairs resulting from continuously varying the decision threshold over the entire range of data observed.

The clinical performance of a laboratory test depends on its diagnostic accuracy, or the ability to correctly classify subjects into clinically relevant subgroups. Diagnostic accuracy measures the test's ability to correctly distinguish two different conditions of the subjects investigated. Such conditions are for example health and disease, latent or recent infection versus no infection, or benign versus malignant disease.

In each case, the ROC plot depicts the overlap between the two distributions by plotting the sensitivity versus 1—specificity for the complete range of decision thresholds. On the y-axis is sensitivity, or the true-positive fraction [defined as (number of true-positive test results) (number of true-positive+number of false-negative test results]. This has also been referred to as positivity in the presence of a disease or condition. It is calculated solely from the affected subgroup. On the x axis is the false-positive fraction, or 1—specificity [defined as (number of false-positive results)/ (number of true-negative+number of false-positive results)]. It is an index of specificity and is calculated entirely from the unaffected subgroup.

Because the true- and false-positive fractions are calculated entirely separately, by using the test results from two different subgroups, the ROC plot is independent of the prevalence of disease in the sample. Each point on the ROC plot represents a sensitivity/-specificity pair corresponding to a particular decision threshold. A test with perfect discrimination (no overlap in the two distributions of results) has an ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45° diagonal line from the lower left corner to the upper right corner. Most plots fall in between these two extremes. (If the ROC plot falls completely below the 45° diagonal, this is easily remedied by reversing the criterion for "positivity" from "greater than" to "less than" or vice versa.) Qualitatively, the closer the plot is to the upper left corner, the higher the overall accuracy of the test.

One convenient goal to quantify the diagnostic accuracy of a laboratory test is to express its performance by a single number. The most common global measure is the area under the ROC plot. By convention, this area is always >0.5 (if it is not, one can reverse the decision rule to make it so). Values range between 1.0 (perfect separation of the test values of the two groups) and 0.5 (no apparent distributional difference between the two groups of test values). The area does not depend only on a particular portion of the plot such as the point closest to the diagonal or the sensitivity at 90% specificity, but on the entire plot. This is a quantitative, descriptive expression of how close the ROC plot is to the perfect one (area=1.0).

Clinical utility of the novel antigen pools may be assessed in comparison to and in combination with other diagnostic tools for the given infection. In the case of infection with *M. tuberculosis* clinical utility of a CMI result may be assessed in comparison to established diagnostic tests such as IGRA or the TST using a receiver operator curve analysis.

Preparation Methods

In general, *M. tuberculosis* antigens, and DNA sequences encoding such antigens, may be prepared using any one of a variety of procedures.

They may be purified as native proteins from the *M. tuberculosis* cell or culture filtrate by procedures such as those described above. Immunogenic antigens may also be produced recombinantly using a DNA sequence encoding the antigen, which has been inserted into an expression vector and expressed in an appropriate host. Examples of host cells are *E. coli*. The polypeptides or immunogenic portion hereof can also be produced synthetically having fewer than about 100 amino acids, and generally fewer than 50 amino acids and may be generated using techniques well known to those ordinarily skilled in the art, such as commercially available solid-phase techniques where amino acids are sequentially added to a growing amino acid chain.

In the construction and preparation of plasmid DNA encoding the polypeptide, a host strain such as *E. coli* can be used. Plasmid DNA can then be prepared from overnight cultures of the host strain carrying the plasmid of interest, and purified using e.g. the Qiagen Giga-Plasmid column kit (Qiagen, Santa Clarita, Calif., USA) including an endotoxin removal step.

Fusion Proteins

Besides being separate entities two or more of the immunogenic polypeptides may also be produced as fusion proteins, by which methods superior characteristics of the polypeptide of the invention can be achieved. For instance, fusion partners that facilitate export of the polypeptide when produced recombinantly, fusion partners that facilitate purification of the polypeptide, and fusion partners that enhance the immunogenicity of the polypeptide fragment of the invention are all interesting possibilities. Therefore, the invention also pertains to a fusion polypeptide comprising at least two (such as 2, 3, 4, 5, 6, 7, 8, 9, 10 or more) polypeptide or immunogenic fragment defined above and optionally at least one additional fusion partner, and to compositions comprising fusion proteins. The fusion partner can, in order to enhance immunogenicity, be another polypeptide derived from *M. tuberculosis*, such as of a polypeptide fragment derived from a bacterium belonging to the tuberculosis complex, such as ESAT-6, TB10.4, CFP10, RD1-ORF2, Rv1036, MPB64, MPT64, Ag85A, Ag85B (MPT59), MPB59, Ag85C, 19 kDa lipoprotein, MPT32 and alpha-crystallin, or at least one T-cell epitope of any of the above mentioned antigens (WO0179274; WO01041519; (Nagai, 1991; Rosenkrands, 1998; Skjot, 2000). The invention also pertains to a fusion polypeptide comprising mutual fusions of two or more (such as 3, 4, 5, 6, 7, 8, 9, 10 or more) of the polypeptides (or immunogenic portions thereof) of the invention.

FIGURE LEGENDS

FIG. 1. Heat map showing immune recognition in 34 volunteer donors from Egypt based on a cut-off of 100 pg/ml of IFN-γ. Two cases had latent TB (subjects 1 and 2) and 32 cases were diagnosed with TB disease (subjects 3-34). White color code indicates no response, grey color code indicates a response, and black color indicates a response to the given antigen with no response to either ESAT-6 or CFP10.

Figure 2:
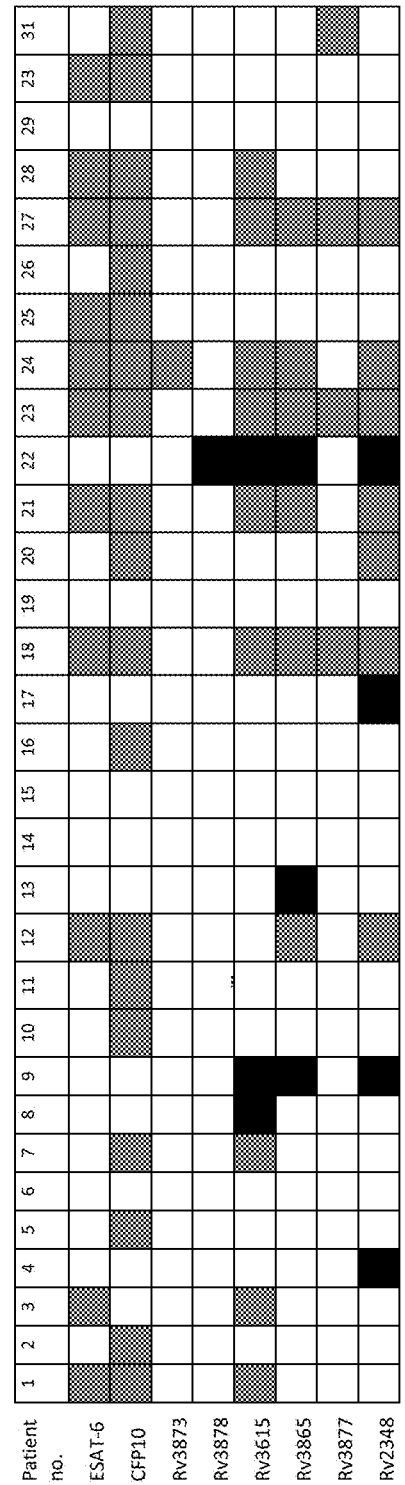

FIG. 2. Heat map showing immune recognition in 31 volunteer donors from Greenland based on a cut-off of 50 pg/ml of IFN-γ. 14 were diagnosed with TB (subjects 1-14) and 17 had latent TB (subjects 15-31). White color code indicates no response, grey color code indicates a response, and black color indicates a response to the given antigen with no response to either ESAT-6 or CFP10.

Figure 3:
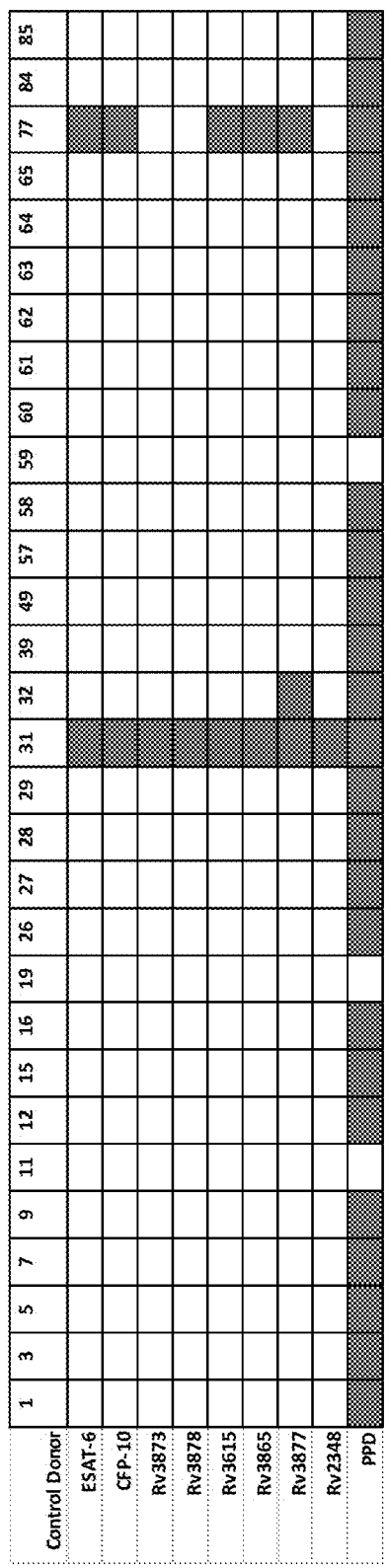

FIG. 3. Heat map showing immune recognition in 30 endemic control donors from Egypt based on a cut-off of 100 pg/ml of IFN-γ. All donors were BCG vaccinated and had no history of TB disease or known contact to a TB patient. Donors were defined as "endemic controls" since they were living in Egypt which is considered an intermediate endemic country. White color code indicates no response and grey color code indicates a response. The investigated antigens were all highly specific in contrast to PPD, which was included as an example of an unspecific antigenic stimulation. Donors 31 and 77 both recognized a broad range of *M. tuberculosis* antigens indicating latent infection in spite of mentioned selection criteria.

Figure 4:
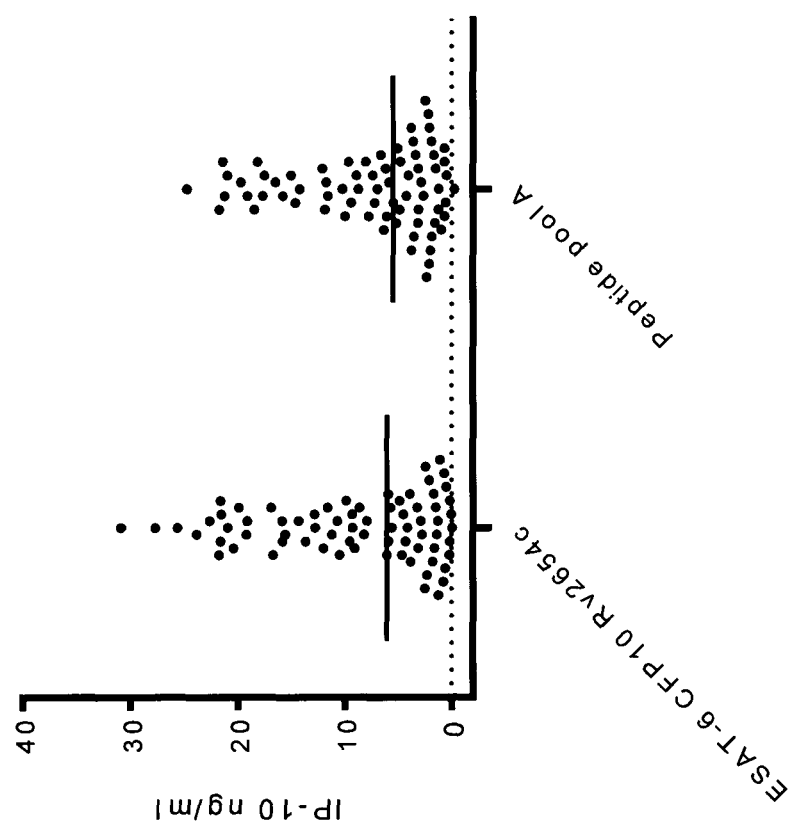

FIG. 4. IP-10 responses to the Quantiferon peptide pool (ESAT-6, CFP10, Rv2654c (peptide 4)) and to the peptide pool A in 73 TB patients from Egypt. Solid lines indicate median responses of 6 ng/ml for Quantiferon antigens and 5.5 ng/ml for peptide pool A.

Figure 5:
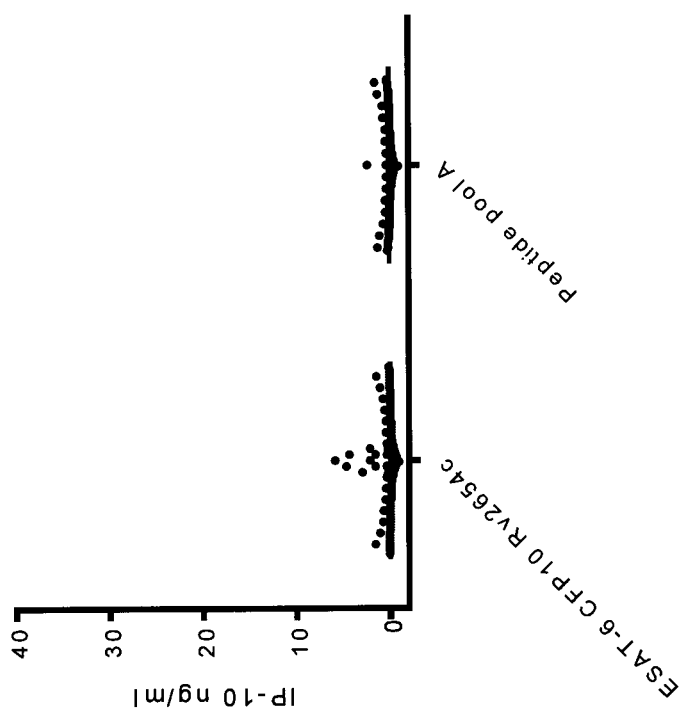

FIG. 5. IP-10 responses to the Quantiferon peptide pool (ESAT-6, CFP10, Rv2654c (peptide 4)) and to peptide pool A in 100 *M. tuberculosis*-unexposed individuals from Denmark. Solid lines indicate median responses of 0 ng/ml for both antigen pools. This shows a high specificity (few false positives) of the whole pool of peptides indicating that each peptide has a high specificity.

Figure 6:
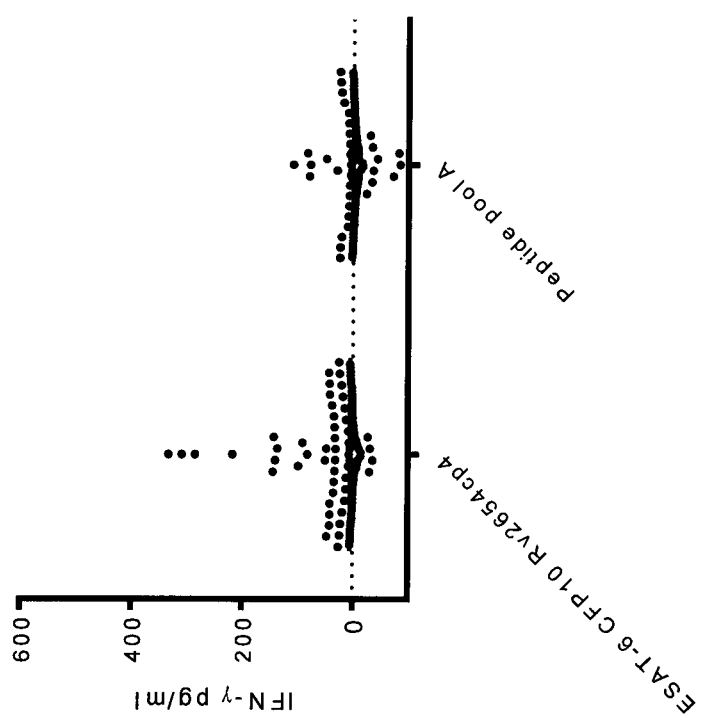

FIG. 6. IFN-γ responses to the Quantiferon peptide pool (ESAT-6, CFP10, Rv2654c (peptide 4)) and peptide pool A in 100 *M. tuberculosis*-unexposed individuals from Denmark. Dotted line indicates a median response of 0 pg/ml for peptide pool A and 4.9 pg/ml for the Quantiferon antigens. This shows a high specificity (few false positives) of the whole pool of peptides indicating that each peptide has a high specificity.

Figure 7:
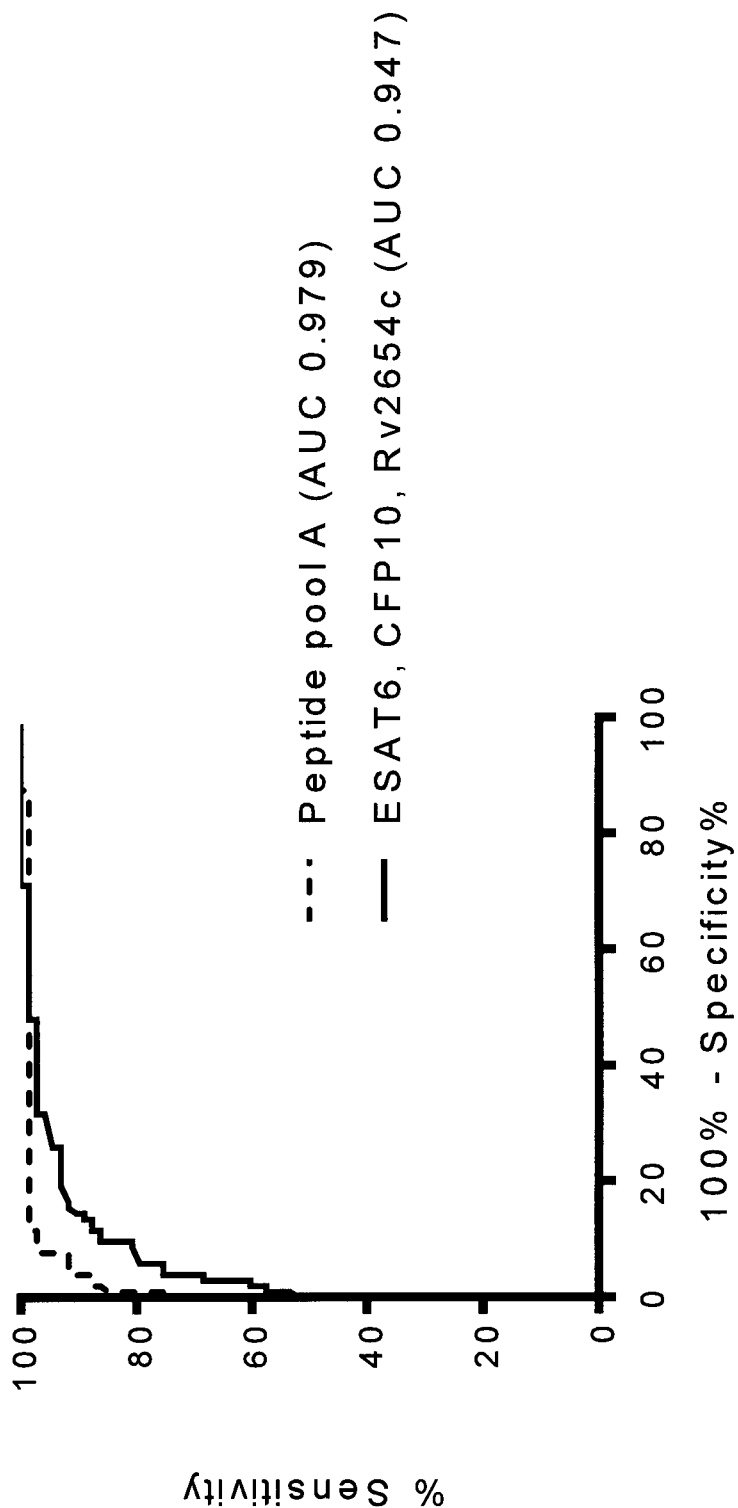

FIG. 7. Receiver operating characteristic (ROC) curve analysis comparing the diagnostic potential of peptide pool A to the Quantiferon antigens in 100 *M. tuberculosis*-unexposed individuals and 73 TB patients. This shows a high specificity (few false positives) of the whole pool of peptides indicating that each peptide has a high specificity.

Figure 8:
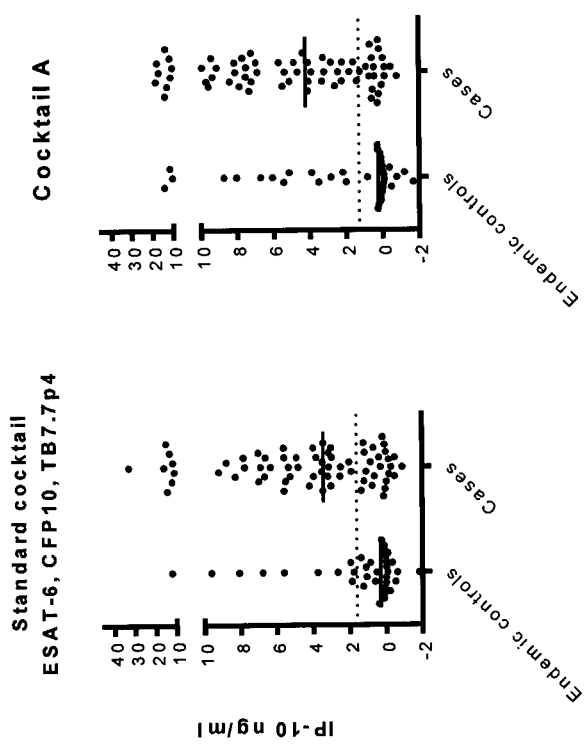

FIG. 8. IP-10 (ng/ml) responses to the Quantiferon peptide pool (ESAT-6, CFP10, and Rv2654c) and to peptide pool A in 68 cases of microbiologically confirmed TB patients and 36 endemic controls from Tanzania.

Figure 9:
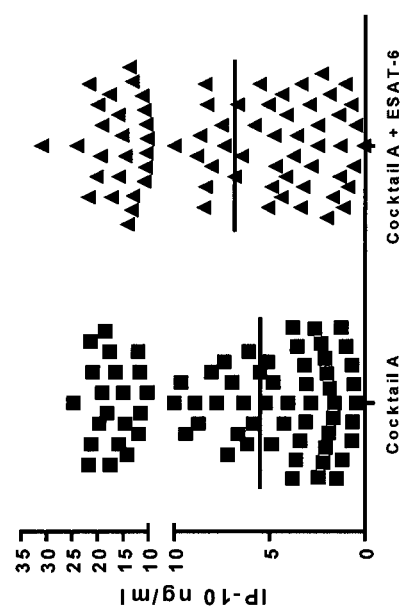

FIG. 9. IP-10 (ng/ml) responses to peptide pool A and peptide pool A enriched with ESAT-6 in 73 patients with confirmed TB from Cairo, Egypt. The line indicates the median.

EXAMPLES

Example 1. Initial Selection of Antigens

T cell antigens selected for the immunodiagnosis of TB should be specific for *M. tuberculosis* infection to avoid interference from vaccination with BCG and most prevalent atypical mycobacteria. At the same time, it is important to avoid ESAT-6 given that ESAT-6 is present in many of the novel vaccines against TB. As described above in Background of the invention, we have through an extensive and strict down-selection process based on theoretical considerations, practical testing and literature search of hundreds of potential antigens selected no more than 9 *M. tuberculosis*-antigens for further testing. These are:

CFP10 (Rv3874).

The 10-kDa culture filtrate antigen is together with ESAT-6 the basis in the current cell-based diagnostic blood tests for *M. tuberculosis* infection by the IFN-γ release assays (IGRAs). CFP10 is an immunodominant *M. tuberculosis* antigen, and the diagnostic specificity of CFP10 and ESAT-6 is caused by their genomic location in region of difference 1 (RD1), a region which is absent in all BCG strains (Behr, 1999) and involved in the pathogenesis of *M. tuberculosis* Genes encoding components of the ESX-1 secretion pathway are also localized in RD1. In a review on interferon-γ assay studies a sensitivity for CFP10 of 61-71% in TB patients was reported (Pai, 2004). In contrast to ESAT-6, CFP10 is not a part of any of the current vaccine candidates under evaluation.

Rv3877.

As for CFP10 the Rv3877 gene is located in the RD1 region on the *M. tuberculosis* chromosome and has no close homologues elsewhere in the *M. tuberculosis* genome. The protein is not present in *M. bovis* BCG or the environmental mycobacterial *M. avium* and can therefore be used for specific *M. tuberculosis* diagnostic without interference from possible prior BCG vaccination or heavy exposure to environmental mycobacteria such as *M. avium*. Rv3877 is a transmembrane protein and a key component of the ESX-1 secretion since it forms the pore that the ESX-1 substrates are secreted through (Abdallah, 2007). A pool of synthetic peptides covering the Rv3877 protein induced positive responses by 33% of PBMC's isolated from human TB patients (Mustafa, 2008).

Rv3614c and Rv3615c.

The espA-espC-espD (Rv3616c-Rv3615c-Rv3614c) gene cluster is essential for ESX-1 dependent protein secretion and *M. tuberculosis* virulence (Fortune, 2005; MacGurn, 2005), and the three genes were recently demonstrated to be co-transcribed (Chen, 2012). Rv3616c and Rv3615c are co-secreted with ESAT-6 and CFP10 (Fortune, 2005; MacGurn, 2005), whereas Rv3614c secretion does not exclusively require ESX-1 functions (Chen, 2012). In cattle, the *M. bovis* counterpart of Rv3615c, Mb3645c, stimulated IFN-γ responses in 37% of *M. bovis* infected animals, but not in naïve and BCG-vaccinated animals (Sidders, 2008). Mb3645c and Rv3615c show 100% amino acid identity. In cattle, the C-terminal part of the Mb3645c protein (amino acids 57-103) was the most immunogenic (Sidders, 2008). In humans, Rv3615c has also been identified as a potential candidate for *M. tuberculosis*-specific T-cell based immunodiagnosis with recognition of TB cases and low response in BCG vaccinated (Millington, 2011). In patients with active TB, the most frequently recognised peptides were located in the C-terminal part of the molecule (amino acids 66-90). Although the gene encoding Rv3615c is present in BCG, the Rv3615c protein is specifically recognised in *M. tuberculosis* infected individuals, but with limited recognition in BCG vaccinated persons.

EspF (Rv3865).

The ESX-1 secretion-associated protein EspF protein or *M. bovis* Mb3895 (identical to Rv3865 from *M. tuberculosis*) was identified by Ewer et al (Ewer, 2006) as a promising diagnostic marker in cattle infected experimentally or naturally with *M. bovis*. Fifty percent of experimentally infected cattle responded to the Mb3895 peptide pool whereas BCG-vaccinated calves did not respond to this peptide pool.

Rv2348c.

Rv2348c is a hypothetical protein with unknown function. The Rv2348c gene is located in the RD7 region. This region has been shown to be absent in BCG (Behr, 1999) and the protein can therefore be used for TB diagnosis without interference from prior BCG vaccination. The gene is highly transcribed in vitro (Arnvig, 2011) and the protein has been identified in proteome studies (de Souza, 2011). The amino acid fragment 23-50 in the Rv2348c ORF (open reading frame) has very high homology to the *M. avium* gene Mav_2040.

Rv3873.

From the amino acid sequence of Rv3873, a region covering amino acids 12-70 was covered by overlapping peptides. Among several RD peptide pools evaluated this pool of Rv3873 peptides, termed Rv3873A, was identified as one of the most promising pools recognised by 46% of PBMCs from TB patients (Brock, 2004). Potential cross-reactive stretches were not present in this part of the molecule.

Rv3878.

As described for Rv3873 above, a peptide pool named Rv3878B, covering amino acids 122-189 of this RD1 protein, was defined and evaluated. It was recognised by 32% of PBMCs from human TB patients, and was suggested as a peptide cocktail or pool which could be combined with ESAT-6 and CFP10 to maximize the sensitivity (Brock, 2004).

Rv2654c.

The Rv2654c gene is encoded by the RD11 region and encodes a possible PhiRv2 prophage protein with unknown function. By screening overlapping peptides covering the entire protein product of Rv2654c (designated TB7.7) Brock et al found no cross-recognition in BCG-vaccinated individuals and furthermore showed a sensitivity of 47% (Brock, 2004). A selected peptide (SEQ ID no 8) is included in the QuantiFERON® TB Gold test.

TABLE 1

Sequence list for the selected peptides.

| Protein | Peptide | SEQ ID NO. |
| --- | --- | --- |
| Rv2654 | P4 | 8 |
| CFP10 (Rv3874) | P1-P6 | 9-14 |
| Rv3615c | P1-P4 | 15-18 |
| Rv3865 | P1-P3 | 19-21 |
| Rv2348c | P1-P4 | 22-25 |
| Rv3614 | P1-P20 | 26-45 |
| Rv3877 | P1-P5 | 46-50 |

Example 2. Selection of Antigens

Seven of the antigens listed in the text above were tested for recognition in TB patients or latently infected individuals in two independent studies in Egypt and Greenland. In both studies, ESAT-6 (Rv3875) was also included as a comparator and benchmark antigen. Furthermore, PPD was included in Egypt as an example of an unspecific antigenic stimulation.

Freshly sampled diluted whole blood was re-stimulated with the selected peptides from the antigens as outlined and the response to peptide-pools of ESAT-6 and CFP10 was included as benchmark.

In the Egypt study 34 volunteer donors (8 females and 26 males) were included as positive controls. Thirty-two of these were diagnosed with TB disease with documented positive sputum culture (subjects 3-34). Two cases had latent TB (subjects 1 and 2). In addition, 30 endemic negative control donors (5 females and 25 males) were included. These were all presumed BCG vaccinated, had no history of TB disease and had had no known contact to a TB patient. In the Greenland study, 31 subjects were included (15 females and 16 males).

Fourteen were diagnosed with TB disease (subjects 1-14); in 11 cases with documented positive sputum culture and in 4 cases the TB diagnosis was done on clinical grounds. The remaining 17 subject had latent TB (subjects 15-31).

In both studies freshly sampled diluted whole blood was stimulated in plates with the selected antigens (10 μg/ml of each peptide). Synthetic peptides (obtained from Genecust) from antigens ESAT-6, CFP10, Rv3873, Rv3878, Rv3615c, Rv3865, Rv3877 and Rv2348c were screened in both studies and positive (PHA) and negative (medium alone) controls and (in Egypt only) PPD were also included (not shown). The diluted whole blood was incubated at 37 degrees Celsius for 5 days, and subsequently supernatants were harvested and tested for (IFN-γ) by an in-house ELISA. A positive response in these studies was defined as an IFN-γ concentration of 100 or 50 pg/ml for the Egypt and Greenland study, respectively.

FIGS. 1, 2 and 3 are graphic representations (heat maps) of data where the individual values contained are represented as colours with white colour showing no response, grey colour indicates a response to the given antigen, and black colour represent a response to an antigen where the same donor do not respond to ESAT-6 and/or CFP10. As shown, several of the test antigens were recognized in TB patients or latently infected donors with the most predominant responses deriving from stimulation with Rv3615c (recognized in 49% of the donors). Importantly, ESAT-6 only recognizes three patients not being recognized upon stimulation with CFP10 (patient no. 9 and 17 in FIG. 1, and patient no. 3 in FIG. 2) and of those Rv3615c is capable of recognizing all three patients. Furthermore, re-stimulation with Rv3615c showed recognition in 11 and 9 donors not recognized by ESAT-6 and CFP10, respectively. In contrast, two of the antigens were recognized in a very limited number of donors; Rv3873 was recognized in merely two out of 65 donors and Rv3878 was recognized in seven of the 65 donors. Thus, despite previous data on these antigens in TB patients from Denmark and the Netherlands with intermediate sensitivity (Rv3873 with 32% for Rv3878 and 46% for Rv3873 (Brock, 2004), the data obtain herein emphasize that not all antigen expected to be sensitive perform in all settings. Rv3865, Rv3877, and Rv2348c showed intermediate sensitivity and was recognized in 16, 12, and 15 of the 65 donors. Importantly, the antigens, Rv3615c, Rv3865, and Rv2348c all give rise to responses in a number of donors which did not recognize ESAT-6 and/or CFP10 further demonstrating the diagnostic potential of these antigens. The specificity of the selected antigens were confirmed in a panel of 30 endemic negative control donor from Egypt (FIG. 3). As shown, the investigated antigens were all highly specific, in contrast to PPD, which was included as an example of an unspecific antigenic stimulation. Donors 31 and 77 both recognized a broad range of M. tuberculosis antigens including both ESAT-6 and CFP-10 strongly indicating latent infection in spite of the mentioned selection criteria.

Example 3. CFP10 and 3615c are comparable to CFP10 and ESAT-6

The diagnostic performance of the combination CFP10 and Rv3615c was subsequently compared to that of the combination CFP10 and ESAT-6. We included whole blood samples from 35 individuals from Greenland of which 18 had a latent M. tuberculosis infection defined as a positive Quantiferon test and/or proven exposure to M. tuberculosis and tuberculin skin test conversion and 17 patients that were microbiologically confirmed TB. Individual aliquots of 200 µl undiluted whole blood was stimulated with overlapping peptides representing CFP10 (SEQ ID 1) or Rv3615c (SEQ ID 15-18) or ESAT-6 (SEQ ID 51) in a final concentration of 5 ug/ml in a humidified 37° C. incubator for 7 days. A negative control sample (nil) was prepared in a parallel. After incubation, the plasma supernatant was isolated and the level of IFN-γ was determined using ELISA.

The diagnostic ability of the three antigens was assessed by adding the measured level of antigen specific production of IFN-γ (level in stimulated whole blood subtracted the level in the unstimulated well) in response to stimulation with individual antigen(s), followed by comparison of this sum to a cut off. The cut off was defined as a combined antigen specific response of at least 50 pg/ml and 4 times higher than the nil value in the individual patient. Antigen specific levels above the cut off classified the individual patient as antigen positive, and antigen specific levels below the cut off as antigen negative.

Table 2 shows the sensitivity of individual antigens CFP10, Rv3615c, ESAT-6 and combinations. As shown, the diagnostic performance of the combination CFP10 and Rv3615c is comparable to that of CFP10 and ESAT-6 with both combinations showing 60% sensitivity. Combining CFP10, Rv3615c and ESAT-6 further improves sensitivity from 60% up to 69%.

TABLE 2

Comparing the sensitivity of CFP10, Rv3615c, and ESAT-6 and combinations hereof.

| Antigen | % sensitivity |
| --- | --- |
| CFP10 | 49 |
| Rv3615c | 34 |
| ESAT-6 | 31 |
| CFP10 + Rv3615c | 60 |
| CFP10 + ESAT-6 | 60 |
| CFP10 + Rv3615c + ESAT-6 | 69 |

Example 4. Enrichment of the Combination CFP10 and Rv3615c with Three Antigens: Rv2348c, Rv3865, and Rv3877

Using the same whole blood samples as above (35 individuals from Greenland; 18 with latent M. tuberculosis infection and 17 patients with microbiologically confirmed TB) and the same assay conditions, we evaluated the effect of combining CFP10 and Rv3615c with three different antigens; Rv2348c, Rv3865, and Rv3877.

The diagnostic ability of the three antigens was assessed by adding the measured level of antigen specific production of IFN-γ (level in stimulated whole blood subtracted the level in the unstimulated well) in response to the individual antigen(s), followed by comparison of the sum to a cut off. The cut off was defined as a combined antigen specific response of at least 50 pg/ml and 4 times higher than the nil value in the individual patient. Antigen specific levels above the cut off classified the individual patient as antigen positive, and antigen specific levels below the cut off as antigen negative.

Table 3 shows the sensitivity of the individual antigens Rv3865, CFP10, Rv3615c and combinations. The sensitivity of Rv3865 is relatively modest with only 20% sensitivity but adding Rv3865 to CFP10 and Rv3615c augments the overall diagnostic sensitivity 6% compared to CFP10 and Rv3865 alone.

TABLE 3

Comparison of CFP10, Rv3615c, Rv3865 and combinations hereof for the diagnosis of M. tuberculosis infection.

| Antigen | % sensitivity |
| --- | --- |
| Rv3865 | 20 |
| CFP10 + Rv3615c | 60 |
| CFP10 + Rv3615c + Rv3865 | 66 |

Similarly, the diagnostic ability of Rv3877 was only 11% but also this antigen enhanced the overall sensitivity of CFP10 and Rv3615c from 60% up to 69% (table 4).

TABLE 4

Comparison of CFP10, Rv3615c, Rv3877 and combinations hereof for the diagnosis of *M. tuberculosis* infection.

| Antigen | % sensitivity |
|---|---|
| Rv3877 | 11 |
| CFP10 + Rv3615c | 60 |
| CFP10 + Rv3615c + Rv3877 | 69 |

Finally, we evaluated whether Rv2348c was also capable of increasing the diagnostic ability of CFP10 and Rv3615c (table 5). As shown, the sensitivity of Rv2348c was 29% and adding Rv2348c to CFP10 and Rv3615c augments the diagnostic sensitivity with 23% compared to when using CFP10 and Rv3615c alone.

TABLE 5

Comparison of CFP10, Rv3615c, Rv2348c and combinations hereof for the diagnosis of *M. tuberculosis* infection.

| Antigen | % sensitivity |
|---|---|
| Rv2348c | 29 |
| CFP10 + Rv3615c | 60 |
| CFP10 + Rv3615c + Rv2348c | 83 |

We selected the following antigens (CFP10, Rv3615c, Rv3865, and Rv2348c) for further evaluation of sensitivity and specificity when combining these 4 antigens into a single peptide pool (peptide pool A).

Example 5. Sensitivity- and Specificity-Testing of Peptide Pool A

It is well known in the field that an immunodiagnostic cocktail comprising ESAT-6, CFP10 and TB7.7p4 is the preferred method for diagnosis infection with *M. tuberculosis*. This antigen cocktail is considered both sensitive and specific, and it forms the basis of the Quantiferon test. As is clear from previous examples, combination of antigens improves diagnostic sensitivity and test reliability as the underlying magnitude of IFN-γ responses is higher and detected more robustly compared to having the antigens alone.

A very user-friendly approach to immunodiagnosis is to use vacutainer tubes precoated with the antigens in a cocktail. E.g. in the Quantiferon test, lyophilized peptides representing the antigen cocktail are coated with heparin in a vacutainer tube. Blood is drawn into this tube allowing for the peptides to interact with antigen-specific CD4 and CD8 T cells. After 16-24 hours incubation the tube is centrifuged and the level of IFN-γ produced can be measured in the plasma supernatant and compared to a negative and positive control samples. Tested subjects can further be classified as either infected or uninfected if the level is above a cut off for positive test result.

It is well known that other immune effector molecules associated with IFN-γ signaling are useful to diagnose *M. tuberculosis* infection (Chego ERJ 2014). The chemokine IP-10 is produced in very high levels and has comparable diagnostic performance to IFN-γ.

To demonstrate the usefulness of combining several antigens into one antigen cocktail, we combined the following antigens into "peptide pool A". Peptide pool A consisted of the following peptides:

CFP10: 6 peptides covering the entire amino acid sequence of CFP10 (SEQ IDs no 9-14)

Rv3615c: 4 peptides covering amino acids 55-103 (SEQ IDs no 15-18)

Rv3865: 3 peptides covering amino acids 9-44 (SEQ IDs no 19-21)

Rv2348c: 4 peptides covering amino acids 56-109 of the full length protein sequence (SEQ IDs no 22-25)

A second and independent study in Egypt was done in order to test the sensitivity of the 4 antigens when combined into peptide pool A. In the study 73 TB patients with documented positive sputum culture were included and each subject donated a blood sample drawn directly into prior prepared antigen coated vacuum tubes. Tubes were coated with either ESAT-6+CFP10+Rv2654c peptides (i.e. same peptides as in the Quantiferon test and used as a benchmark, designated Quantiferon peptide pool) or with peptide pool A (CFP10+Rv3516c+Rv3865+Rv2348c as indicated above). After 16-24 hours of incubation, supernatants were collected and tested for release of the cytokine IP-10 with an in-house ELISA assay. As shown in FIG. 4, a high proportion of the TB patients recognized both peptide pool A as well as the Quantiferon peptide pool. Median responses were 5.5 ng/ml of IP10 for peptide pool A and 6.0 for Quantiferon peptide pool.

In parallel, an independent study was done in Denmark in order to test the specificity of the peptide pool A. In the study, 100 subjects living in a very low TB prevalence area (Denmark) and with no known exposure to *M. tuberculosis* were included. In 17 cases, subjects were documented BCG vaccinated, and in 19 cases the BCG vaccination status was unknown/undocumented. The remaining participants were not BCG vaccinated. Similar to the sensitivity study fresh whole blood was drawn directly into vacuum tubes pre-coated with either peptide pool A (CFP10+Rv3615c+Rv3865+Rv2348c) or the benchmark Quantiferon peptide pool (ESAT-6+CFP10+Rv2654c). After 16-24 hours of incubation, supernatants were collected and tested for the content of the cytokines IP-10 and IFN-γ with an in-house ELISA assay. Although median IP-10 responses to peptide pool A and the Quantiferon peptide pool were both 0 ng/ml (FIG. 5), a few non-exposed donors exhibited positive responses upon re-stimulation with the Quantiferon-antigens with IP-10 levels of approximately 5 ng/ml. The same trend with non-exposed donors showing false positive responses was observed when analysing secretion of IFN-γ (FIG. 6; peptide pool A median of 0 pg/ml, inter quartile range (IQR) of −0.5-5.2 pg/ml and Quantiferon peptide pool median 4.9 pg/ml, IQR −0.6-32.45 pg/ml.

Combining the data from the sensitivity and specificity studies allowed us to perform a Receiver operating characteristic (ROC) curve analysis comparing the diagnostic potential of peptide pool A to the Quantiferon antigen pool (FIG. 7). The area under the curve (AUC) was 0.979 for peptide pool A and 0.947 for the Quantiferon antigen pool. By ROC curve analysis the optimal cut-offs for both peptide pool A and Quantiferon peptide pool were identified as 1.4 ng/ml for peptide pool A (sensitivity 87, 7% at 98.1% specificity); and 2.3 ng/ml for Quantiferon peptide pool (sensitivity 75.3% at 96.2% specificity).

Using these cut-offs we compared head-to-head the number of positive and negative responses upon re-stimulation with the Quantiferon peptide pool and the peptide pool A (Table 6 and 7). Of the 73 TB patients, 54 (74%) recognized the Quantiferon peptide pools which is within the range published on the sensitivity of the Quantiferon antigens between 64-89% (Dewan, 2007). In comparison, the peptide pool A recognized a higher proportion of the TB patients in this study (64 of the 73 patients) corresponding to an estimated sensitivity of 88%. Using a McNemar's test, peptide pool A demonstrated a significantly higher sensitivity in this study compared to the Quantiferon peptide pool ($p<0.012$).

TABLE 6

Head to head comparison of Quantiferon peptide pool and peptide pool A in 73 TB patients.

| | | Peptide pool A | | |
|---|---|---|---|---|
| | | Negative | Positive | Total |
| Quantiferon antigen pool | Negative | 6 | 13 | 19 |
| | Positive | 3 | 51 | 54 |
| | Total | 9 | 64 | 73 |

TABLE 7

Head to head comparison of Quantiferon peptide pool and peptide pool A in 100 presumed uninfected controls.

| | | Peptide pool A | | |
|---|---|---|---|---|
| | | Negative | Positive | Total |
| Quantiferon antigen pool | Negative | 95 | 1 | 96 |
| | Positive | 2 | 2 | 4 |
| | Total | 97 | 3 | 100 |

In conclusion, peptide pool A exhibited a significantly higher sensitivity (more true positives; table 6) compared to the Quantiferon antigens and furthermore was as least as specific (comparable false positives; table 7). These results clearly demonstrates that it is possible to 1) design TB-diagnostic peptide pools devoid of ESAT-6 with a higher sensitivity compared to the current Quantiferon antigens, 2) design a non-ESAT-6 containing antigen pool with a specificity comparable to current Quantiferon.

Example 6. Validation of Peptide Pool A

It is well known to the skilled addressee that validation of cut offs for immunodiagnostic tests requires confirmation in independent cohorts. For this end, we included 68 cases of microbiologically confirmed TB patients and 36 endemic controls i.e. individuals of which some have preexisting but controlled *M. tuberculosis* infection from Tanzania.

From each donor, 1 ml blood was drawn into 5 vacutainer tubes comprising lyophilized heparin (18 IU) and peptides (5 ug/peptide) as follows: Quantiferon peptide pool (ESAT-6, CFP10 and TB7.7p4 (tube 1), comparable to Quantiferon test); peptide pool A (CFP10, Rv3615c, Rv3865 and Rv2348B (tube 2)) and a negative control tube (tube 3).

In FIG. 8 we show the negative control tube (tube 3) subtracted IP-10 (ng/ml) responses in cases and controls from tube 1 and tube 2. It is evident that the Quantiferon peptide pool and peptide pool A are comparable in terms of the high magnitude of response in TB cases. As expected, the endemic control responses are more heterogeneous underpinning that some tested individuals are infected.

Using the pre-defined cut off identified in Example 5 (1.4 ng/ml), the diagnostic accuracy was compared both for TB patients (table 8) and endemic controls (table 9). In the TB patient group the diagnostic sensitivity of the standard Quantiferon peptide pool was 66% (45 defined as positive of 68 patients included) and higher for peptide pool A with 72% sensitivity (49 defined as positive of the 68 patients). As expected, the agreement between the two tests was very high with 91% accordance (44 being positive in both tests, 18 being negative in both tests with an overall accordance of 62 out of 68).

TABLE 8

Agreement between Quantiferon peptide pool and peptide pool A after classifying responses to antigen stimulation from 68 patients with confirmed TB using predetermined cut offs for positive test.

| | | Quantiferon peptide pool | | |
|---|---|---|---|---|
| TB patients | | Positive | Negative | Sum |
| Peptide pool A | Positive | 44 | 5 | 49 |
| | Negative | 1 | 18 | 19 |
| | Sum | 45 | 23 | 68 |

In the endemic control population there is no gold standard for infection therefore we present the rate as positive responders. Peptide pool A detected 39% (14/36) as positive and the standard Quantiferon peptide pool 31% (11/36) again suggesting higher sensitivity. The agreement was also very high (92% corresponding to accordance in 33 cases out of 36 included).

TABLE 9

Agreement between Quantiferon peptide pool and peptide pool A after classifying responses to antigen stimulation from 36 endemic controls using predetermined cut offs for positive test.

| | | Quantiferon peptide pool | | |
|---|---|---|---|---|
| TB patients | | Positive | Negative | Sum |
| Peptide pool A | Positive | 11 | 0 | 11 |
| | Negative | 3 | 22 | 25 |
| | Sum | 14 | 22 | 36 |

Example 7. Peptide Pool A can be Further Improved when Combined with ESAT-6

We further assessed the possibility of adding ESAT-6 to peptide pool A with the purpose of improving the diagnostic performance even further. We therefore tested peptide pool A+ESAT-6 and peptide pool A in the cohort of 73 cases of confirmed TB in Cairo, Egypt and using the same assay conditions as described in example 5. In FIG. 9 it is evident that the magnitude of responses is increased when combining peptide pool A with ESAT-6 with peptide pool A having a median response of 5.50 ng/ml of IP-10 compared to peptide pool A with ESAT-6 where the median is 6.86 ng/ml IP-10. Using a cut-off of 0.75 ng/ml we compared the responder frequencies in the two groups. In peptide pool A, the responder frequency was 93% with 68 being positive of the 73 tested patients whereas the frequency for peptide pool A with ESAT-6 was 96% (70 of 73 patients—96%). Thus, combining the peptide pool A with ESAT-6 reduced the false negative rate from 7% to 4%.

REFERENCES

Abdallah, A. M., N. C. Gey van Pittius, et al. (2007). Type VII secretion—mycobacteria show the way. *Nature reviews. Microbiology* 5(11): 883-891.

Aggerbeck, H., R. Giemza, et al. (2013). Randomised clinical trial investigating the specificity of a novel skin test (C-Tb) for diagnosis of *M. tuberculosis* infection. *PloS one* 8(5): e64215.

Albrethsen, J., J. Agner, et al. (2013). Proteomic profiling of *Mycobacterium tuberculosis* identifies nutrient-starvation-responsive toxin-antitoxin systems. *Molecular & cellular proteomics: MCP* 12(5): 1180-1191.

Andersen, P. (1994). Effective vaccination of mice against *Mycobacterium tuberculosis* infection with a soluble mixture of secreted mycobacterial proteins. *Infection and immunity* 62(6): 2536-2544.

Andersen, P., M. E. Munk, et al. (2000). Specific immune-based diagnosis of tuberculosis. *Lancet* 356(9235): 1099-1104.

Arnvig, K. B., I. Comas, et al. (2011). Sequence-based analysis uncovers an abundance of non-coding RNA in the total transcriptome of *Mycobacterium tuberculosis*. *PLoS pathogens* 7(11): e1002342.

Behr, M. A., M. A. Wilson, et al. (1999). Comparative genomics of BCG vaccines by whole-genome DNA microarray. *Science* 284(5419): 1520-1523.

Biselli, R., S. Mariotti, et al. (2010). Detection of interleukin-2 in addition to interferon-γ discriminates active tuberculosis patients, latently infected individuals, and controls. *Clinical Microbiology and Infection* 16(8): 1282-1284.

Brock, I., K. Weldingh, et al. (2004). Specific T-cell epitopes for immunoassay-based diagnosis of *Mycobacterium tuberculosis* infection. *Journal of clinical microbiology* 42(6): 2379-2387.

Chen, J. M., S. Boy-Rottger, et al. (2012). EspD is critical for the virulence-mediating ESX-1 secretion system in *Mycobacterium tuberculosis*. *Journal of bacteriology* 194(4): 884-893.

de Souza, G. A., M. O. Arntzen, et al. (2011). Proteogenomic analysis of polymorphisms and gene annotation divergences in prokaryotes using a clustered mass spectrometry-friendly database. *Molecular & cellular proteomics: MCP* 10(1): M110 002527.

Deenadayalan, A., D. Heaslip, et al. (2010). Immunoproteomic identification of human T cell antigens of *Mycobacterium tuberculosis* that differentiate healthy contacts from tuberculosis patients. *Molecular & cellular proteomics: MCP* 9(3): 538-549.

Dewan, P. K., J. Grinsdale, et al. (2007). Low Sensitivity of a Whole-Blood Interferon-γ Release Assay for Detection of Active Tuberculosis. *Clinical Infectious Diseases* 44(1): 69-73.

Ewer, K., P. Cockle, et al. (2006). Antigen mining with iterative genome screens identifies novel diagnostics for the *Mycobacterium tuberculosis* complex. *Clinical and vaccine immunology: CVI* 13(1): 90-97.

Fortune, S. M., A. Jaeger, et al. (2005). Mutually dependent secretion of proteins required for mycobacterial virulence. *Proceedings of the National Academy of Sciences of the United States of America* 102(30): 10676-10681.

Hall, L. J., S. Clare, et al. (2009). Characterisation of a live *Salmonella* vaccine stably expressing the *Mycobacterium tuberculosis* Ag85B-ESAT-6ESAT-6 fusion protein. *Vaccine* 27(49): 6894-6904.

Harboe, M., A. S. Malin, et al. (1998). B-cell epitopes and quantification of the ESAT-6 protein of *Mycobacterium tuberculosis*. *Infection and immunity* 66(2): 717-723.

Kilgus, J., T. Jardetzky, et al. (1991). Analysis of the permissive association of a malaria T cell epitope with DR molecules. *The Journal of Immunology* 146(1): 307-315.

Liu, X. Q., D. Dosanjh, et al. (2004). Evaluation of T-cell responses to novel RD1- and RD2-encoded *Mycobacterium tuberculosis* gene products for specific detection of human tuberculosis infection. *Infection and immunity* 72(5): 2574-2581.

Lustig, J. V., H. L. Rieger, et al. (1976). Humoral and cellular responses to native antigen following oral and parenteral immunization with lipid-conjugated bovine serum albumin. *Cellular immunology* 24(1): 164-172.

MacGurn, J. A., S. Raghavan, et al. (2005). A non-RD1 gene cluster is required for Snm secretion in *Mycobacterium tuberculosis*. *Molecular microbiology* 57(6): 1653-1663.

Merrifield, R. B. (1963). Solid Phase Peptide Synthesis. I. The Synthesis of a Tetrapeptide. *Journal of the American Chemical Society* 85(14): 2149-2154.

Millington, K. A., S. M. Fortune, et al. (2011). Rv3615c is a highly immunodominant RD1 (Region of Difference 1)-dependent secreted antigen specific for *Mycobacterium tuberculosis* infection. *Proceedings of the National Academy of Sciences of the United States of America* 108(14): 5730-5735.

Moon, H. W. and M. Hur (2013). Interferon-gamma release assays for the diagnosis of latent tuberculosis infection: an updated review. *Annals of clinical and laboratory science* 43(2): 221-229.

Mowat, A. M., A. M. Donachie, et al. (1991). Immune-stimulating complexes containing Quil A and protein antigen prime class I MHC-restricted T lymphocytes in vivo and are immunogenic by the oral route. *Immunology* 72(3): 317-322.

Mustafa, A. S., R. Al-Attiyah, et al. (2008). Efficient testing of large pools of *Mycobacterium tuberculosis* RD1 peptides and identification of major antigens and immunodominant peptides recognized by human Th1 cells. *Clinical and vaccine immunology: CVI* 15(6): 916-924.

Nagai, S., H. G. Wiker, et al. (1991). Isolation and partial characterization of major protein antigens in the culture fluid of *Mycobacterium tuberculosis*. *Infection and immunity* 59(1): 372-382.

Pai, M., L. W. Riley, et al. (2004). Interferon-gamma assays in the immunodiagnosis of tuberculosis: a systematic review. *The Lancet infectious diseases* 4(12): 761-776.

Pearson, W. R. and D. J. Lipman (1988). Improved tools for biological sequence comparison. *Proceedings of the National Academy of Sciences* 85(8): 2444-2448.

Ravn, P., A. Demissie, et al. (1999). Human T Cell Responses to the ESAT-6 Antigen from *Mycobacterium tuberculosis*. *Journal of Infectious Diseases* 179(3): 637-645.

Redelman-Sidi, G. and K. A. Sepkowitz (2013). IFN-gamma release assays in the diagnosis of latent tuberculosis infection among immunocompromised adults. *American journal of respiratory and critical care medicine* 188(4): 422-431.

Rosenkrands, I., P. B. Rasmussen, et al. (1998). Identification and characterization of a 29-kilodalton protein from *Mycobacterium tuberculosis* culture filtrate recognized by mouse memory effector cells. *Infection and immunity* 66(6): 2728-2735.

Ruhwald, M. and P. Ravn (2009). Biomarkers of latent TB infection. *Expert review of respiratory medicine* 3(4): 387-401.

Schopfer, K., H. L. Rieder, et al. (2013). The sensitivity of an interferon-gamma release assay in microbiologically confirmed pediatric tuberculosis. *European journal of pediatrics*.

Sester, U., M. Fousse, et al. (2011). Whole-Blood Flow-Cytometric Analysis of Antigen-Specific CD4 T-Cell Cytokine Profiles Distinguishes Active Tuberculosis from Non-Active States. *PloS one* 6(3): e17813.

Sidders, B., C. Pirson, et al. (2008). Screening of highly expressed mycobacterial genes identifies Rv3615c as a useful differential diagnostic antigen for the *Mycobacterium tuberculosis* complex. *Infection and immunity* 76(9): 3932-3939.

Sinigaglia, F., M. Guttinger, et al. (1988). A malaria T-cell epitope recognized in association with most mouse and human MHC class II molecules. *Nature* 336(6201): 778-780.

Skjot, R. L., T. Oettinger, et al. (2000). Comparative evaluation of low-molecular-mass proteins from *Mycobacterium tuberculosis* identifies members of the ESAT-6 family as immunodominant T-cell antigens. *Infection and immunity* 68(1): 214-220.

Sonnenberg, P., J. R. Glynn, et al. (2005). How soon after infection with HIV does the risk of tuberculosis start to increase? A retrospective cohort study in South African gold miners. *The Journal of infectious diseases* 191(2): 150-158.

Stryhn, A., L. Ø. Pedersen, et al. (1996). Peptide binding specificity of major histocompatibility complex class I resolved into an array of apparently independent subspecificities: quantitation by peptide libraries and improved prediction of binding. *European Journal of Immunology* 26(8): 1911-1918.

Thompson, J. D., D. G. Higgins, et al. (1994). CLUSTAL W: improving the sensitivity of progressive multiple sequence alignment through sequence weighting, position-specific gap penalties and weight matrix choice. *Nucleic Acids Research* 22(22): 4673-4680.

van Dissel, J. T., S. M. Arend, et al. (2010). Ag85B-ESAT-6 adjuvanted with IC31 promotes strong and long-lived *Mycobacterium tuberculosis* specific T cell responses in naive human volunteers. *Vaccine* 28(20): 3571-3581.

van Dissel, J. T., D. Soonawala, et al. (2011). Ag85B-ESAT-6 adjuvanted with IC31(R) promotes strong and long-lived *Mycobacterium tuberculosis* specific T cell responses in volunteers with previous BCG vaccination or tuberculosis infection. *Vaccine* 29(11): 2100-2109.

Xu, Y., W. Liu, et al. (2009). Recombinant *Mycobacterium bovis* BCG expressing the chimeric protein of antigen 85B and ESAT-6 enhances the Th1 cell-mediated response. *Clinical and vaccine immunology: CVI* 16(8): 1121-1126.

Yang, X., L. Bao, et al. (2011). A novel recombinant *Mycobacterium bovis bacillus* Calmette-Guerin strain expressing human granulocyte macrophage colony-stimulating factor and *Mycobacterium tuberculosis* early secretory antigenic target 6 complex augments Th1 immunity. *Acta biochimica et biophysica Sinica* 43(7): 511-518.

Young, F., J. A. Critchley, et al. (2009). A review of co-morbidity between infectious and chronic disease in Sub Saharan Africa: TB and diabetes mellitus, HIV and metabolic syndrome, and the impact of globalization. *Globalization and health* 5: 9.

Zhang, H., P. Peng, et al. (2010). Recombinant *Mycobacterium smegmatis* expressing an ESAT-6ESAT-6-CFP10 fusion protein induces anti-mycobacterial immune responses and protects against *Mycobacterium tuberculosis* challenge in mice. *Scandinavian journal of immunology* 72(4): 349-357.

Zweig, M. H. and G. Campbell (1993). Receiver-operating characteristic (ROC) plots: a fundamental evaluation tool in clinical medicine. *Clinical chemistry* 39(4): 561-577.

Aagaard, C., I. Brock, et al. (2004). Mapping immune reactivity toward Rv2653 and Rv2654: two novel low-molecular-mass antigens found specifically in the *Mycobacterium tuberculosis* complex. *The Journal of infectious diseases* 189(5): 812-819.

Aagaard, C., T. Hoang, et al. (2011). A multistage tuberculosis vaccine that confers efficient protection before and after exposure. *Nature medicine* 17(2): 189-194.

---

The invention claimed is:

1. A diagnostic composition comprising a mixture of substantially pure polypeptides comprised of amino acid sequences selected from
   a) Rv3874 (SEQ ID NO: 1), Rv3615c (SEQ ID NO: 2), and Rv2348c (SEQ ID NO: 4);
   b) at least one fragment of Rv3874 (SEQ ID NO: 1), at least one fragment of Rv3615c (SEQ ID NO: 2), and at least one fragment of Rv2348c (SEQ ID NO: 4), said fragments comprising immunogenic epitopes from said amino acid sequences, wherein said fragments are substantially pure; and
   c) i) an amino acid sequence having at least 80% sequence identity to SEQ ID NO: 1 and at the same time being immunogenic, an amino acid sequence having at least 80% sequence identity to SEQ ID NO: 2 and at the same time being immunogenic, and an amino acid sequence having at least 80% identity to SEQ ID NO: 4 and at the same time being immunogenic; or
      ii) an amino acid sequence having at least 80% sequence identity to a fragment of SEQ ID NO: 1 and at the same time being immunogenic, an amino acid sequence having at least 80% sequence identity to a fragment of SEQ ID NO: 2 and at the same time being immunogenic, and an amino acid sequence having at least 80% sequence identity to a fragment of SEQ ID NO: 4 and at the same time being immunogenic, wherein said amino acid sequences are substantially pure.

2. A diagnostic composition according to claim 1, comprising Rv3874 (SEQ ID NO: 1), Rv3615c (SEQ ID NO: 2) and Rv2348c (SEQ ID NO: 4) or fragments comprising immunogenic epitopes hereof, wherein said fragments are substantially pure.

3. A diagnostic composition according to claim 1 wherein the fragments comprising immunogenic epitopes of SEQ ID NO: 1 are selected from SEQ ID NOS: 9-14.

4. A diagnostic composition according to claim 1 wherein the fragments comprising immunogenic epitopes of SEQ ID NO: 2 are selected from SEQ ID NOS: 15-18 and SEQ ID NOS: 59-63.

5. A diagnostic composition according to claim 1 wherein the fragments comprising immunogenic epitopes of SEQ ID NO: 4 are selected from SEQ ID NOS: 22-25.

6. A diagnostic composition according to claim 1, wherein the fragments comprising immunogenic epitopes from said polypeptides are present as overlapping peptides of at least 10 amino acid length.

7. A diagnostic composition according to claim 1, wherein some or all of the polypeptides or fragments comprising immunogenic epitopes are fused together optionally via linkers or spacers.

8. A method of in vitro or in vivo diagnosing tuberculosis caused by virulent mycobacteria in an animal using a diagnostic composition according to claim 1.

9. The method according to claim 8 wherein said animal is a human.

10. The method according to claim 8 where said virulent mycobacteria is *Mycobacterium tuberculosis*.

11. The method according to claim 8 where said virulent mycobacteria is *Mycobacterium bovis*.

12. The method according to claim 8 where said virulent mycobacteria is *Mycobacterium africanum*.

13. The diagnostic composition according to claim 2, comprising Rv3874 (SEQ ID NO: 1), Rv3615c (SEQ ID NO: 2) and Rv2348c (SEQ ID NO: 4).

14. The diagnostic composition according to claim 2, comprising fragments comprising immunogenic epitopes of Rv3874 (SEQ ID NO: 1), Rv3615c (SEQ ID NO: 2) and Rv2348c (SEQ ID NO: 4), wherein said fragments are substantially pure.

15. The diagnostic composition according to claim 1, comprising an amino acid sequence having at least 80% sequence identity to SEQ ID NO: 1 and at the same time being immunogenic, an amino acid sequence having at least 80% sequence identity to SEQ ID NO: 2 and at the same time being immunogenic, and an amino acid sequence having at least 80% identity to SEQ ID NO: 4 and at the same time being immunogenic, wherein said amino acid sequences are substantially pure.

16. The diagnostic composition according to claim 1, comprising an amino acid sequence having at least 80% sequence identity to a fragment of SEQ ID NO: 1 and at the same time being immunogenic, an amino acid sequence having at least 80% sequence identity to a fragment of SEQ ID NO: 2 and at the same time being immunogenic, and an amino acid sequence having at least 80% sequence identity to a fragment of SEQ ID NO: 4 and at the same time being immunogenic, wherein said fragments are substantially pure.

* * * * *

SEQUENCE LISTING

```
<160> NUMBER OF SEQ ID NOS: 63

<210> SEQ ID NO 1
<211> LENGTH: 100
<212> TYPE: PRT
<213> ORGANISM: Mycobacterium tuberculosis

<400> SEQUENCE: 1

Met Ala Glu Met Lys Thr Asp Ala Ala Thr Leu Ala Gln Glu Ala Gly
1               5                   10                  15

Asn Phe Glu Arg Ile Ser Gly Asp Leu Lys Thr Gln Ile Asp Gln Val
            20                  25                  30

Glu Ser Thr Ala Gly Ser Leu Gln Gly Gln Trp Arg Gly Ala Ala Gly
        35                  40                  45

Thr Ala Ala Gln Ala Ala Val Val Arg Phe Gln Glu Ala Ala Asn Lys
    50                  55                  60

Gln Lys Gln Glu Leu Asp Glu Ile Ser Thr Asn Ile Arg Gln Ala Gly
65                  70                  75                  80

Val Gln Tyr Ser Arg Ala Asp Glu Glu Gln Gln Gln Ala Leu Ser Ser
                85                  90                  95

Gln Met Gly Phe
            100
```

```
<210> SEQ ID NO 2
<211> LENGTH: 103
<212> TYPE: PRT
<213> ORGANISM: Mycobacterium tuberculosis

<400> SEQUENCE: 2

Met Thr Glu Asn Leu Thr Val Gln Pro Glu Arg Leu Gly Val Leu Ala
1               5                   10                  15

Ser His His Asp Asn Ala Ala Val Asp Ala Ser Ser Gly Val Glu Ala
            20                  25                  30

Ala Ala Gly Leu Gly Glu Ser Val Ala Ile Thr His Gly Pro Tyr Cys
        35                  40                  45

Ser Gln Phe Asn Asp Thr Leu Asn Val Tyr Leu Thr Ala His Asn Ala
    50                  55                  60

Leu Gly Ser Ser Leu His Thr Ala Gly Val Asp Leu Ala Lys Ser Leu
65                  70                  75                  80

Arg Ile Ala Ala Lys Ile Tyr Ser Glu Ala Asp Glu Ala Trp Arg Lys
                85                  90                  95

Ala Ile Asp Gly Leu Phe Thr
            100

<210> SEQ ID NO 3
<211> LENGTH: 103
<212> TYPE: PRT
<213> ORGANISM: Mycobacterium tuberculosis

<400> SEQUENCE: 3

Met Thr Gly Phe Leu Gly Val Val Pro Ser Phe Leu Lys Val Leu Ala
1               5                   10                  15

Gly Met His Asn Glu Ile Val Gly Asp Ile Lys Arg Ala Thr Asp Thr
            20                  25                  30

Val Ala Gly Ile Ser Gly Arg Val Gln Leu Thr His Gly Ser Phe Thr
        35                  40                  45

Ser Lys Phe Asn Asp Thr Leu Gln Glu Phe Glu Thr Thr Arg Ser Ser
    50                  55                  60

Thr Gly Thr Gly Leu Gln Gly Val Thr Ser Gly Leu Ala Asn Asn Leu
65                  70                  75                  80

Leu Ala Ala Ala Gly Ala Tyr Leu Lys Ala Asp Asp Gly Leu Ala Gly
                85                  90                  95

Val Ile Asp Lys Ile Phe Gly
            100

<210> SEQ ID NO 4
<211> LENGTH: 108
<212> TYPE: PRT
<213> ORGANISM: Mycobacterium tuberculosis

<400> SEQUENCE: 4

Met Leu Leu Pro Leu Gly Pro Pro Leu Pro Asp Ala Val Val Ala
1               5                   10                  15

Lys Arg Ala Glu Ser Gly Met Leu Gly Gly Leu Ser Val Pro Leu Ser
            20                  25                  30

Trp Gly Val Ala Val Pro Pro Asp Asp Tyr Asp His Trp Ala Pro Ala
        35                  40                  45

Pro Glu Asp Gly Ala Asp Val Asp Val Gln Ala Ala Glu Gly Ala Asp
    50                  55                  60
```

```
Ala Glu Ala Ala Ala Met Asp Glu Trp Asp Glu Trp Gln Ala Trp Asn
 65                  70                  75                  80

Glu Trp Val Ala Glu Asn Ala Glu Pro Arg Phe Glu Val Pro Arg Ser
                 85                  90                  95

Ser Ser Ser Val Ile Pro His Ser Pro Ala Ala Gly
            100                 105
```

```
<210> SEQ ID NO 5
<211> LENGTH: 184
<212> TYPE: PRT
<213> ORGANISM: Mycobacterium tuberculosis

<400> SEQUENCE: 5

Val Asp Leu Pro Gly Asn Asp Phe Asp Ser Asn Asp Phe Asp Ala Val
  1               5                  10                  15

Asp Leu Trp Gly Ala Asp Gly Ala Glu Gly Trp Thr Ala Asp Pro Ile
                 20                  25                  30

Ile Gly Val Gly Ser Ala Ala Thr Pro Asp Thr Gly Pro Asp Leu Asp
             35                  40                  45

Asn Ala His Gly Gln Ala Glu Thr Asp Thr Glu Gln Glu Ile Ala Leu
 50                  55                  60

Phe Thr Val Thr Asn Pro Pro Arg Thr Val Ser Val Ser Thr Leu Met
 65                  70                  75                  80

Asp Gly Arg Ile Asp His Val Glu Leu Ser Ala Arg Val Ala Trp Met
                 85                  90                  95

Ser Glu Ser Gln Leu Ala Ser Glu Ile Leu Val Ile Ala Asp Leu Ala
            100                 105                 110

Arg Gln Lys Ala Gln Ser Ala Gln Tyr Ala Phe Ile Leu Asp Arg Met
            115                 120                 125

Ser Gln Gln Val Asp Ala Asp Glu His Arg Val Ala Leu Leu Arg Lys
130                 135                 140

Thr Val Gly Glu Thr Trp Gly Leu Pro Ser Pro Glu Glu Ala Ala Ala
145                 150                 155                 160

Ala Glu Ala Glu Val Phe Ala Thr Arg Tyr Ser Asp Asp Cys Pro Ala
                165                 170                 175

Pro Asp Asp Glu Ser Asp Pro Trp
            180
```

```
<210> SEQ ID NO 6
<211> LENGTH: 81
<212> TYPE: PRT
<213> ORGANISM: Mycobacterium tuberculosis

<400> SEQUENCE: 6

Met Ser Gly His Ala Leu Ala Ala Arg Thr Leu Leu Ala Ala Ala Asp
  1               5                  10                  15

Glu Leu Val Gly Gly Pro Pro Val Glu Ala Ser Ala Ala Ala Leu Ala
                 20                  25                  30

Gly Asp Ala Ala Gly Ala Trp Arg Thr Ala Ala Val Glu Leu Ala Arg
             35                  40                  45

Ala Leu Val Arg Ala Val Ala Glu Ser His Gly Val Ala Ala Val Leu
 50                  55                  60

Phe Ala Ala Thr Ala Ala Ala Ala Ala Val Asp Arg Gly Asp Pro
 65                  70                  75                  80

Pro
```

-continued

```
<210> SEQ ID NO 7
<211> LENGTH: 511
<212> TYPE: PRT
<213> ORGANISM: Mycobacterium tuberculosis

<400> SEQUENCE: 7

Met Ser Ala Pro Ala Val Ala Ala Gly Pro Thr Ala Gly Ala Thr
1               5                   10                  15

Ala Ala Arg Pro Ala Thr Thr Arg Val Thr Ile Leu Thr Gly Arg Arg
            20                  25                  30

Met Thr Asp Leu Val Leu Pro Ala Ala Val Pro Met Glu Thr Tyr Ile
                35                  40                  45

Asp Asp Thr Val Ala Val Leu Ser Glu Val Leu Glu Asp Thr Pro Ala
50                  55                  60

Asp Val Leu Gly Gly Phe Asp Phe Thr Ala Gln Gly Val Trp Ala Phe
65                  70                  75                  80

Ala Arg Pro Gly Ser Pro Pro Leu Lys Leu Asp Gln Ser Leu Asp Asp
                85                  90                  95

Ala Gly Val Val Asp Gly Ser Leu Leu Thr Leu Val Ser Val Ser Arg
            100                 105                 110

Thr Glu Arg Tyr Arg Pro Leu Val Glu Asp Val Ile Asp Ala Ile Ala
        115                 120                 125

Val Leu Asp Glu Ser Pro Glu Phe Asp Arg Thr Ala Leu Asn Arg Phe
130                 135                 140

Val Gly Ala Ala Ile Pro Leu Leu Thr Ala Pro Val Ile Gly Met Ala
145                 150                 155                 160

Met Arg Ala Trp Trp Glu Thr Gly Arg Ser Leu Trp Trp Pro Leu Ala
                165                 170                 175

Ile Gly Ile Leu Gly Ile Ala Val Leu Val Gly Ser Phe Val Ala Asn
            180                 185                 190

Arg Phe Tyr Gln Ser Gly His Leu Ala Glu Cys Leu Leu Val Thr Thr
        195                 200                 205

Tyr Leu Leu Ile Ala Thr Ala Ala Leu Ala Val Pro Leu Pro Arg
210                 215                 220

Gly Val Asn Ser Leu Gly Ala Pro Gln Val Ala Gly Ala Ala Thr Ala
225                 230                 235                 240

Val Leu Phe Leu Thr Leu Met Thr Arg Gly Gly Pro Arg Lys Arg His
                245                 250                 255

Glu Leu Ala Ser Phe Ala Val Ile Thr Ala Ile Ala Val Ile Ala Ala
            260                 265                 270

Ala Ala Ala Phe Gly Tyr Gly Tyr Gln Asp Trp Val Pro Ala Gly Gly
        275                 280                 285

Ile Ala Phe Gly Leu Phe Ile Val Thr Asn Ala Ala Lys Leu Thr Val
        290                 295                 300

Ala Val Ala Arg Ile Ala Leu Pro Pro Ile Pro Val Pro Gly Glu Thr
305                 310                 315                 320

Val Asp Asn Glu Glu Leu Leu Asp Pro Val Ala Thr Pro Glu Ala Thr
                325                 330                 335

Ser Glu Glu Thr Pro Thr Trp Gln Ala Ile Ala Ser Val Pro Ala
            340                 345                 350

Ser Ala Val Arg Leu Thr Glu Arg Ser Lys Leu Ala Lys Gln Leu Leu
        355                 360                 365

Ile Gly Tyr Val Thr Ser Gly Thr Leu Ile Leu Ala Ala Gly Ala Ile
        370                 375                 380
```

Ala Val Val Val Arg Gly His Phe Phe Val His Ser Leu Val Ala
385                 390                 395                 400

Gly Leu Ile Thr Thr Val Cys Gly Phe Arg Ser Arg Leu Tyr Ala Glu
            405                 410                 415

Arg Trp Cys Ala Trp Ala Leu Leu Ala Ala Thr Val Ala Ile Pro Thr
        420                 425                 430

Gly Leu Thr Ala Lys Leu Ile Ile Trp Tyr Pro His Tyr Ala Trp Leu
        435                 440                 445

Leu Leu Ser Val Tyr Leu Thr Val Ala Leu Val Ala Leu Val Val Val
        450                 455                 460

Gly Ser Met Ala His Val Arg Arg Val Ser Pro Val Val Lys Arg Thr
465                 470                 475                 480

Leu Glu Leu Ile Asp Gly Ala Met Ile Ala Ala Ile Ile Pro Met Leu
            485                 490                 495

Leu Trp Ile Thr Gly Val Tyr Asp Thr Val Arg Asn Ile Arg Phe
        500                 505                 510

<210> SEQ ID NO 8
<211> LENGTH: 18
<212> TYPE: PRT
<213> ORGANISM: Mycobacterium tuberculosis

<400> SEQUENCE: 8

Ala Trp Arg Thr Ala Ala Val Glu Leu Ala Arg Ala Leu Val Arg Ala
1               5                   10                  15

Val Ala

<210> SEQ ID NO 9
<211> LENGTH: 25
<212> TYPE: PRT
<213> ORGANISM: Mycobacterium tuberculosis

<400> SEQUENCE: 9

Met Ala Glu Met Lys Thr Asp Ala Ala Thr Leu Ala Gln Glu Ala Gly
1               5                   10                  15

Asn Phe Glu Arg Ile Ser Gly Asp Leu
            20                  25

<210> SEQ ID NO 10
<211> LENGTH: 25
<212> TYPE: PRT
<213> ORGANISM: Mycobacterium tuberculosis

<400> SEQUENCE: 10

Gly Asn Phe Glu Arg Ile Ser Gly Asp Leu Lys Thr Gln Ile Asp Gln
1               5                   10                  15

Val Glu Ser Thr Ala Gly Ser Leu Gln
            20                  25

<210> SEQ ID NO 11
<211> LENGTH: 26
<212> TYPE: PRT
<213> ORGANISM: Mycobacterium tuberculosis

<400> SEQUENCE: 11

Asp Gln Val Glu Ser Thr Ala Gly Ser Leu Gln Gly Gln Trp Arg Gly
1               5                   10                  15

Ala Ala Gly Thr Ala Ala Gln Ala Ala Val
            20                  25

<210> SEQ ID NO 12
<211> LENGTH: 25
<212> TYPE: PRT
<213> ORGANISM: Mycobacterium tuberculosis

<400> SEQUENCE: 12

Ala Ala Gly Thr Ala Ala Gln Ala Ala Val Val Arg Phe Gln Glu Ala
1               5                   10                  15

Ala Asn Lys Gln Lys Gln Glu Leu Asp
            20                  25

<210> SEQ ID NO 13
<211> LENGTH: 25
<212> TYPE: PRT
<213> ORGANISM: Mycobacterium tuberculosis

<400> SEQUENCE: 13

Ala Ala Asn Lys Gln Lys Gln Glu Leu Asp Glu Ile Ser Thr Asn Ile
1               5                   10                  15

Arg Gln Ala Gly Val Gln Tyr Ser Arg
            20                  25

<210> SEQ ID NO 14
<211> LENGTH: 25
<212> TYPE: PRT
<213> ORGANISM: Mycobacterium tuberculosis

<400> SEQUENCE: 14

Ile Arg Gln Ala Gly Val Gln Tyr Ser Arg Ala Asp Glu Glu Gln Gln
1               5                   10                  15

Gln Ala Leu Ser Ser Gln Met Gly Phe
            20                  25

<210> SEQ ID NO 15
<211> LENGTH: 20
<212> TYPE: PRT
<213> ORGANISM: Mycobacterium tuberculosis

<400> SEQUENCE: 15

Leu Asn Val Tyr Leu Thr Ala His Asn Ala Leu Gly Ser Ser Leu His
1               5                   10                  15

Thr Ala Gly Val
            20

<210> SEQ ID NO 16
<211> LENGTH: 20
<212> TYPE: PRT
<213> ORGANISM: Mycobacterium tuberculosis

<400> SEQUENCE: 16

Leu Gly Ser Ser Leu His Thr Ala Gly Val Asp Leu Ala Lys Ser Leu
1               5                   10                  15

Arg Ile Ala Ala
            20

<210> SEQ ID NO 17
<211> LENGTH: 20
<212> TYPE: PRT
<213> ORGANISM: Mycobacterium tuberculosis

```
<400> SEQUENCE: 17

Asp Leu Ala Lys Ser Leu Arg Ile Ala Ala Lys Ile Tyr Ser Glu Ala
1               5                   10                  15

Asp Glu Ala Trp
            20

<210> SEQ ID NO 18
<211> LENGTH: 19
<212> TYPE: PRT
<213> ORGANISM: Mycobacterium tuberculosis

<400> SEQUENCE: 18

Lys Ile Tyr Ser Glu Ala Asp Glu Ala Trp Arg Lys Ala Ile Asp Gly
1               5                   10                  15

Leu Phe Thr

<210> SEQ ID NO 19
<211> LENGTH: 20
<212> TYPE: PRT
<213> ORGANISM: Mycobacterium tuberculosis

<400> SEQUENCE: 19

Pro Ser Phe Leu Lys Val Leu Ala Gly Met His Asn Glu Ile Val Gly
1               5                   10                  15

Asp Ile Lys Arg
            20

<210> SEQ ID NO 20
<211> LENGTH: 20
<212> TYPE: PRT
<213> ORGANISM: Mycobacterium tuberculosis

<400> SEQUENCE: 20

Gly Met His Asn Glu Ile Val Gly Asp Ile Lys Arg Ala Thr Asp Thr
1               5                   10                  15

Val Ala Gly Ile
            20

<210> SEQ ID NO 21
<211> LENGTH: 20
<212> TYPE: PRT
<213> ORGANISM: Mycobacterium tuberculosis

<400> SEQUENCE: 21

Asp Ile Lys Arg Ala Thr Asp Thr Val Ala Gly Ile Ser Gly Arg Val
1               5                   10                  15

Gln Leu Thr His
            20

<210> SEQ ID NO 22
<211> LENGTH: 20
<212> TYPE: PRT
<213> ORGANISM: Mycobacterium tuberculosis

<400> SEQUENCE: 22

Asp Val Gln Ala Ala Glu Gly Ala Asp Ala Glu Ala Ala Ala Met Asp
1               5                   10                  15

Glu Trp Asp Glu
            20
```

<210> SEQ ID NO 23
<211> LENGTH: 20
<212> TYPE: PRT
<213> ORGANISM: Mycobacterium tuberculosis

<400> SEQUENCE: 23

Ala Ala Ala Met Asp Glu Trp Asp Glu Trp Gln Ala Trp Asn Glu Trp
1               5                   10                  15

Val Ala Glu Asn
            20

<210> SEQ ID NO 24
<211> LENGTH: 20
<212> TYPE: PRT
<213> ORGANISM: Mycobacterium tuberculosis

<400> SEQUENCE: 24

Ala Trp Asn Glu Trp Val Ala Glu Asn Ala Glu Pro Arg Phe Glu Val
1               5                   10                  15

Pro Arg Ser Ser
            20

<210> SEQ ID NO 25
<211> LENGTH: 20
<212> TYPE: PRT
<213> ORGANISM: Mycobacterium tuberculosis

<400> SEQUENCE: 25

Pro Arg Phe Glu Val Pro Arg Ser Ser Ser Ser Val Ile Pro His Ser
1               5                   10                  15

Pro Ala Ala Gly
            20

<210> SEQ ID NO 26
<211> LENGTH: 18
<212> TYPE: PRT
<213> ORGANISM: Mycobacterium tuberculosis

<400> SEQUENCE: 26

Val Asp Leu Pro Gly Asn Asp Phe Asp Ser Asn Asp Phe Asp Ala Val
1               5                   10                  15

Asp Leu

<210> SEQ ID NO 27
<211> LENGTH: 18
<212> TYPE: PRT
<213> ORGANISM: Mycobacterium tuberculosis

<400> SEQUENCE: 27

Ser Asn Asp Phe Asp Ala Val Asp Leu Trp Gly Ala Asp Gly Ala Glu
1               5                   10                  15

Gly Trp

<210> SEQ ID NO 28
<211> LENGTH: 18
<212> TYPE: PRT
<213> ORGANISM: Mycobacterium tuberculosis

<400> SEQUENCE: 28

Trp Gly Ala Asp Gly Ala Glu Gly Trp Thr Ala Asp Pro Ile Ile Gly
1               5                   10                  15

Val Gly

<210> SEQ ID NO 29
<211> LENGTH: 18
<212> TYPE: PRT
<213> ORGANISM: Mycobacterium tuberculosis

<400> SEQUENCE: 29

Thr Ala Asp Pro Ile Ile Gly Val Gly Ser Ala Ala Thr Pro Asp Thr
1 5 10 15

Gly Pro

<210> SEQ ID NO 30
<211> LENGTH: 18
<212> TYPE: PRT
<213> ORGANISM: Mycobacterium tuberculosis

<400> SEQUENCE: 30

Ser Ala Ala Thr Pro Asp Thr Gly Pro Asp Leu Asp Asn Ala His Gly
1 5 10 15

Gln Ala

<210> SEQ ID NO 31
<211> LENGTH: 18
<212> TYPE: PRT
<213> ORGANISM: Mycobacterium tuberculosis

<400> SEQUENCE: 31

Asp Leu Asp Asn Ala His Gly Gln Ala Glu Thr Asp Thr Glu Gln Glu
1 5 10 15

Ile Ala

<210> SEQ ID NO 32
<211> LENGTH: 18
<212> TYPE: PRT
<213> ORGANISM: Mycobacterium tuberculosis

<400> SEQUENCE: 32

Glu Thr Asp Thr Glu Gln Glu Ile Ala Leu Phe Thr Val Thr Asn Pro
1 5 10 15

Pro Arg

<210> SEQ ID NO 33
<211> LENGTH: 18
<212> TYPE: PRT
<213> ORGANISM: Mycobacterium tuberculosis

<400> SEQUENCE: 33

Leu Phe Thr Val Thr Asn Pro Pro Arg Thr Val Ser Val Ser Thr Leu
1 5 10 15

Met Asp

<210> SEQ ID NO 34
<211> LENGTH: 18
<212> TYPE: PRT
<213> ORGANISM: Mycobacterium tuberculosis

<400> SEQUENCE: 34

Thr Val Ser Val Ser Thr Leu Met Asp Gly Arg Ile Asp His Val Glu
1 5 10 15

Leu Ser

<210> SEQ ID NO 35
<211> LENGTH: 18
<212> TYPE: PRT
<213> ORGANISM: Mycobacterium tuberculosis

<400> SEQUENCE: 35

```
Gly Arg Ile Asp His Val Glu Leu Ser Ala Arg Val Ala Trp Met Ser
1               5                   10                  15

Glu Ser
```

<210> SEQ ID NO 36
<211> LENGTH: 18
<212> TYPE: PRT
<213> ORGANISM: Mycobacterium tuberculosis

<400> SEQUENCE: 36

```
Ala Arg Val Ala Trp Met Ser Glu Ser Gln Leu Ala Ser Glu Ile Leu
1               5                   10                  15

Val Ile
```

<210> SEQ ID NO 37
<211> LENGTH: 18
<212> TYPE: PRT
<213> ORGANISM: Mycobacterium tuberculosis

<400> SEQUENCE: 37

```
Gln Leu Ala Ser Glu Ile Leu Val Ile Ala Asp Leu Ala Arg Gln Lys
1               5                   10                  15

Ala Gln
```

<210> SEQ ID NO 38
<211> LENGTH: 18
<212> TYPE: PRT
<213> ORGANISM: Mycobacterium tuberculosis

<400> SEQUENCE: 38

```
Ala Asp Leu Ala Arg Gln Lys Ala Gln Ser Ala Gln Tyr Ala Phe Ile
1               5                   10                  15

Leu Asp
```

<210> SEQ ID NO 39
<211> LENGTH: 18
<212> TYPE: PRT
<213> ORGANISM: Mycobacterium tuberculosis

<400> SEQUENCE: 39

```
Ser Ala Gln Tyr Ala Phe Ile Leu Asp Arg Met Ser Gln Gln Val Asp
1               5                   10                  15

Ala Asp
```

<210> SEQ ID NO 40
<211> LENGTH: 18
<212> TYPE: PRT
<213> ORGANISM: Mycobacterium tuberculosis

<400> SEQUENCE: 40

```
Arg Met Ser Gln Gln Val Asp Ala Asp Glu His Arg Val Ala Leu Leu
1               5                   10                  15

Arg Lys
```

```
<210> SEQ ID NO 41
<211> LENGTH: 18
<212> TYPE: PRT
<213> ORGANISM: Mycobacterium tuberculosis

<400> SEQUENCE: 41

Glu His Arg Val Ala Leu Leu Arg Lys Thr Val Gly Glu Thr Trp Gly
1               5                   10                  15

Leu Pro

<210> SEQ ID NO 42
<211> LENGTH: 18
<212> TYPE: PRT
<213> ORGANISM: Mycobacterium tuberculosis

<400> SEQUENCE: 42

Thr Val Gly Glu Thr Trp Gly Leu Pro Ser Pro Glu Glu Ala Ala Ala
1               5                   10                  15

Ala Glu

<210> SEQ ID NO 43
<211> LENGTH: 18
<212> TYPE: PRT
<213> ORGANISM: Mycobacterium tuberculosis

<400> SEQUENCE: 43

Ser Pro Glu Glu Ala Ala Ala Ala Glu Ala Glu Val Phe Ala Thr Arg
1               5                   10                  15

Tyr Ser

<210> SEQ ID NO 44
<211> LENGTH: 18
<212> TYPE: PRT
<213> ORGANISM: Mycobacterium tuberculosis

<400> SEQUENCE: 44

Ala Glu Val Phe Ala Thr Arg Tyr Ser Asp Asp Cys Pro Ala Pro Asp
1               5                   10                  15

Asp Glu

<210> SEQ ID NO 45
<211> LENGTH: 13
<212> TYPE: PRT
<213> ORGANISM: Mycobacterium tuberculosis

<400> SEQUENCE: 45

Asp Asp Cys Pro Ala Pro Asp Asp Glu Ser Asp Pro Trp
1               5                   10

<210> SEQ ID NO 46
<211> LENGTH: 20
<212> TYPE: PRT
<213> ORGANISM: Mycobacterium tuberculosis

<400> SEQUENCE: 46

Ala Val Pro Leu Pro Arg Gly Val Asn Ser Leu Gly Ala Pro Gln Val
1               5                   10                  15

Ala Gly Ala Ala
            20
```

```
<210> SEQ ID NO 47
<211> LENGTH: 20
<212> TYPE: PRT
<213> ORGANISM: Mycobacterium tuberculosis

<400> SEQUENCE: 47

Gly Ala Pro Gln Val Ala Gly Ala Ala Thr Ala Val Leu Phe Leu Thr
1               5                   10                  15

Leu Met Thr Arg
            20

<210> SEQ ID NO 48
<211> LENGTH: 20
<212> TYPE: PRT
<213> ORGANISM: Mycobacterium tuberculosis

<400> SEQUENCE: 48

Val Leu Phe Leu Thr Leu Met Thr Arg Gly Gly Pro Arg Lys Arg His
1               5                   10                  15

Glu Leu Ala Ser
            20

<210> SEQ ID NO 49
<211> LENGTH: 20
<212> TYPE: PRT
<213> ORGANISM: Mycobacterium tuberculosis

<400> SEQUENCE: 49

Pro Arg Lys Arg His Glu Leu Ala Ser Phe Ala Val Ile Thr Ala Ile
1               5                   10                  15

Ala Val Ile Ala
            20

<210> SEQ ID NO 50
<211> LENGTH: 21
<212> TYPE: PRT
<213> ORGANISM: Mycobacterium tuberculosis

<400> SEQUENCE: 50

Val Ile Thr Ala Ile Ala Val Ile Ala Ala Ala Ala Phe Gly Tyr
1               5                   10                  15

Gly Tyr Gln Asp Trp
            20

<210> SEQ ID NO 51
<211> LENGTH: 95
<212> TYPE: PRT
<213> ORGANISM: Mycobacterium tuberculosis

<400> SEQUENCE: 51

Met Thr Glu Gln Gln Trp Asn Phe Ala Gly Ile Glu Ala Ala Ala Ser
1               5                   10                  15

Ala Ile Gln Gly Asn Val Thr Ser Ile His Ser Leu Leu Asp Glu Gly
            20                  25                  30

Lys Gln Ser Leu Thr Lys Leu Ala Ala Ala Trp Gly Gly Ser Gly Ser
        35                  40                  45

Glu Ala Tyr Gln Gly Val Gln Gln Lys Trp Asp Ala Thr Ala Thr Glu
    50                  55                  60
```

```
Leu Asn Asn Ala Leu Gln Asn Leu Ala Arg Thr Ile Ser Glu Ala Gly
 65                  70                  75                  80

Gln Ala Met Ala Ser Thr Glu Gly Asn Val Thr Gly Met Phe Ala
                 85                  90                  95

<210> SEQ ID NO 52
<211> LENGTH: 20
<212> TYPE: PRT
<213> ORGANISM: Mycobacterium tuberculosis

<400> SEQUENCE: 52

Met Thr Glu Gln Gln Trp Asn Phe Ala Gly Ile Glu Ala Ala Ala Ser
 1               5                  10                  15

Ala Ile Gln Gly
            20

<210> SEQ ID NO 53
<211> LENGTH: 16
<212> TYPE: PRT
<213> ORGANISM: Mycobacterium tuberculosis

<400> SEQUENCE: 53

Gly Ile Glu Ala Ala Ala Ser Ala Ile Gln Gly Asn Val Thr Ser Ile
 1               5                  10                  15

<210> SEQ ID NO 54
<211> LENGTH: 25
<212> TYPE: PRT
<213> ORGANISM: Mycobacterium tuberculosis

<400> SEQUENCE: 54

Ser Ala Ile Gln Gly Asn Val Thr Ser Ile His Ser Leu Leu Asp Glu
 1               5                  10                  15

Gly Lys Gln Ser Leu Thr Lys Leu Ala
            20                  25

<210> SEQ ID NO 55
<211> LENGTH: 25
<212> TYPE: PRT
<213> ORGANISM: Mycobacterium tuberculosis

<400> SEQUENCE: 55

Glu Gly Lys Gln Ser Leu Thr Lys Leu Ala Ala Ala Trp Gly Gly Ser
 1               5                  10                  15

Gly Ser Glu Ala Tyr Gln Gly Val Gln
            20                  25

<210> SEQ ID NO 56
<211> LENGTH: 25
<212> TYPE: PRT
<213> ORGANISM: Mycobacterium tuberculosis

<400> SEQUENCE: 56

Ser Gly Ser Glu Ala Tyr Gln Gly Val Gln Gln Lys Trp Asp Ala Thr
 1               5                  10                  15

Ala Thr Glu Leu Asn Asn Ala Leu Gln
            20                  25

<210> SEQ ID NO 57
<211> LENGTH: 25
<212> TYPE: PRT
<213> ORGANISM: Mycobacterium tuberculosis
```

```
<400> SEQUENCE: 57

Thr Ala Thr Glu Leu Asn Asn Ala Leu Gln Asn Leu Ala Arg Thr Ile
1               5                   10                  15

Ser Glu Ala Gly Gln Ala Met Ala Ser
            20                  25

<210> SEQ ID NO 58
<211> LENGTH: 25
<212> TYPE: PRT
<213> ORGANISM: Mycobacterium tuberculosis

<400> SEQUENCE: 58

Thr Ala Thr Glu Leu Asn Asn Ala Leu Gln Asn Leu Ala Arg Thr Ile
1               5                   10                  15

Ser Glu Ala Gly Gln Ala Met Ala Ser
            20                  25

<210> SEQ ID NO 59
<211> LENGTH: 20
<212> TYPE: PRT
<213> ORGANISM: Mycobacterium tuberculosis

<400> SEQUENCE: 59

Val Tyr Leu Thr Ala His Asn Ala Leu Gly Ser Ser Leu His Thr Ala
1               5                   10                  15

Gly Val Asp Leu
            20

<210> SEQ ID NO 60
<211> LENGTH: 20
<212> TYPE: PRT
<213> ORGANISM: Mycobacterium tuberculosis

<400> SEQUENCE: 60

Leu Gly Ser Ser Leu His Thr Ala Gly Val Asp Leu Ala Lys Ser Leu
1               5                   10                  15

Arg Ile Ala Ala
            20

<210> SEQ ID NO 61
<211> LENGTH: 20
<212> TYPE: PRT
<213> ORGANISM: Mycobacterium tuberculosis

<400> SEQUENCE: 61

Gly Val Asp Leu Ala Lys Ser Leu Arg Ile Ala Ala Lys Ile Tyr Ser
1               5                   10                  15

Glu Ala Asp Glu
            20

<210> SEQ ID NO 62
<211> LENGTH: 20
<212> TYPE: PRT
<213> ORGANISM: Mycobacterium tuberculosis

<400> SEQUENCE: 62

Arg Ile Ala Ala Lys Ile Tyr Ser Glu Ala Asp Glu Ala Trp Arg Lys
1               5                   10                  15

Ala Ile Asp Gly
            20
```

```
<210> SEQ ID NO 63
<211> LENGTH: 20
<212> TYPE: PRT
<213> ORGANISM: Mycobacterium tuberculosis

<400> SEQUENCE: 63

Ala Lys Ile Tyr Ser Glu Ala Asp Glu Ala Trp Arg Lys Ala Ile Asp
1               5                   10                  15

Gly Leu Phe Thr
            20
```